US006994971B1

(12) United States Patent
Straume et al.

(10) Patent No.: US 6,994,971 B1
(45) Date of Patent: Feb. 7, 2006

(54) PARTICLE ANALYSIS ASSAY FOR BIOMOLECULAR QUANTIFICATION

(75) Inventors: Tore Straume, Salt Lake City, UT (US); Gang Liu, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 130 days.

(21) Appl. No.: 10/089,560

(22) PCT Filed: Oct. 10, 2000

(86) PCT No.: PCT/US00/27883

§ 371 (c)(1),
(2), (4) Date: Apr. 1, 2002

(87) PCT Pub. No.: WO01/27328

PCT Pub. Date: Apr. 19, 2001

Related U.S. Application Data

(60) Provisional application No. 60/158,664, filed on Oct. 8, 1999.

(51) Int. Cl.
*C12Q 1/68* (2006.01)
*G01N 33/53* (2006.01)

(52) U.S. Cl. .......................................... 435/6; 435/7.1
(58) Field of Classification Search .................. 435/6, 435/7.1
See application file for complete search history.

(56) References Cited

U.S. PATENT DOCUMENTS 5,731,153 A    3/1998  Lucas et al. .................... 435/6
5,741,650 A    4/1998  Lapidus et al. ................. 435/6
5,783,387 A    7/1998  Lucas et al. .................... 435/6
6,027,879 A    2/2000  Lucas et al. .................... 435/6

FOREIGN PATENT DOCUMENTS

| EP | 304845 | 3/1989 |
| JP | 281230 A2 * | 10/1993 |
| WO | WO 86/07387 | 12/1986 |
| WO | WO 00/55363 | 9/2000 |

OTHER PUBLICATIONS

Ahern (The Scientist, vol. 9, No. 15, p. 20, Jul. 1995; Internet copy of article provided in 5 pages, obtained Dec. 22, 1998 at www.the-scientist.library.upenn.edu/yr1995/july/tools_950724.html).*

Vlieger, A.M., et al. "Quantitation of Polymerase Chain Reaction Products by Hydbridization-Based Assays with Fluorescent, Colormetric, or Chemiluminescent Detection.", Analytical Biochemistry 205, 1-7 (1992).

* cited by examiner

*Primary Examiner*—Juliet C. Switzer
(74) *Attorney, Agent, or Firm*—Madson & Metcalf

(57) ABSTRACT

A method is provided for carrying out multi-step separations of objects bearing at least two binding sites. In the first step, a first binder/bead composition is bound to objects that bear the first binding site, and then unbound objects, i.e. objects not bearing the first binding site, are separated from bound objects. In the second step, a second binder/bead composition is bound to the remaining objects that bear the second binding site, and then the objects that are bound to both beads are removed from those objects that are bound to only one bead. The beads can differ in magnetic responsiveness, charge, size, color, and the like, and these differences can be used to carry out the separation steps.

5 Claims, 16 Drawing Sheets

TNGTTCTCCAGCTTGCATGCCTGCAGGTCGACGCCCCTAGATCTCTCTCCTAAAATGGCTCCCCAGACACAGCACAGTGT
                              SalI
ACAAGAGGTCGAACGTACGGACGTCCAGCTGCGGGGATCTAGACACACCATTTTACCGAGGGGTCTGTGTCGTGTCACA

TCCTGGGGTCGTTCAGGACGGAAGGCAGCGGCGCCCCCCCCCAATCTTTGCATGTCTTGGGATGCAAAACAATTTCCCCA
AGGACCCCAGCAAGTCCTGCCTTCCGTCGCCGCGGGGGGGGGTTAGAAACGTACAGAACCCTACGTTTTGTTAAAGGGGT

CCTTCTCTCTGCTCACCCCACCGACCGTCGCCCCTAAAGTGAAGTCTGCTGGCTGCCGAAAAGGGAAATGGAAAGGAGGA
GGAAGAGAGACGAGTGGGGTGGCTGGCAGCGGGGATTTCACTTCAGACGACCGACGGCTTTTCCCTTTACCTTTCCTCCT
ACCATTCAAGTTCAACGACATGGCGACGGCAGCTCCGGCGGGAGCCGCGCTTTGGCAGGGGAGGCTGCGCCATCTGCAGC
TGGTAAGTTCAAGTTGCTGTACCGCTGCCGTCGAGGCCGCCCTCGGCGCGAAACCGTCCCCTCCCACGCGGTAGACGTCG

AGCGCGCTAGCACATAGGGGAAGGGGCGATGGGCCCCCCTCCACGCCTTAGCGTGCAACTCGCCCCCATATTCTCCCCAC
TCGCGCGATCGTGTATCCCCTTCCCCGCTACCCGGGGGGAGGTGCGGAATCGCACGTTGAGCGGGGGTATAAGAGGGGTG

AGCATTCATCCTTGACCCAACCCGCTTTGCTCTTTAGCCCCAGCTCTCTGCTTTGGTCATCACCCCGAAAACCCATGAAA
TCGTAAGTAGGAACTGGGTTGGGCGAAACGAGAAATCGGGGTCGAGAGACGAAACCAGTAGTGGGGCTTTTGGGTACTTT

ATCCACAGCCCCTGCACCCGCGCGTTCCGCTAGAGAACCTACCGTGAAGACCCGAGCGTTGTGTCCTTGTCCTTGCTTAT
TAGGTGTCGGGGACGTGGGCGCGCAAGGCGATCTCTTGGATGGCACTTCTGGGCTCGCAACACAGGAACAGGAACGAATA

TCGATCCTACTTGAAACACTGGGAGCACTCACGGCCTTCGGGGCTCGGCCAGCAGCTTCCGAGAACGATAGCTTTCTTGC
AGCTAGGATGAACTTTGTGACCCTCGTGAGTGCCGGAAGCCCCGAGCCGGTCGTCGAAGGCTCTTGCTATCGAAAGAACG

GCAGCGCGTAGACGCGATGCGGTAATTTTGAGCCACCCAAGATAAGACACTAACTTGACCTTAACTTTGTCAGGGCGCCC
CGTCGCGCATCTGCGCTACGCCATTAAAACTCGGTGGGTTCTATTCTGTGATTGAACTGGAATTGAAACAGTCCCGCGGG

CTGGTATCTGGAGAACGTGAACAGACACTTGTCTGGCAGCTTCTCGTAAAAACTGACTGGGGAAGGGATTCTGAGTCATT
GACCATAGACCTCTTGCACTTGTCTGTGAACAGACCGTCGAAGAGCATTTTTGACTGACCCCTTCCCTAAGACTCAGTAA

TCATTTATTACCCCTTACAAGTTTTGCAAGAAAAGCNTTTTCTTCCTTGNCCAAACTTTAATTATTTTATTGCTCNTTTT
AGTAAATAATGGGGAATGTTCAAAACGTTCTTTTCGAAAAGAAGGAACGGTTTGAAATTAATAAAATAACGAGAAAATCC
CGAGGGGTCTGTGTCGTGTCACAAGGACCCCAGCAAGTCCTGCCTTCCGT-5'                (1)
GACGAGTGGGGTGGCTGGCAGCGGGGATTTCACTTCAGACGACCGACGGC-5'                (2)
TCGAGGCCGCCCTCGGCGCGAAACCGTCCCCTCCCACGCGGTAGACGTCG-5'                (3)
ACGTTGAGCGGGGGTATAAGAGGGGTGTCGTAAGTAGGAACTGGGTTGGG-5'                (4)

Fig 4A

TTNNNNTTNTTCGNCTCGGTACCCGGGGATCCTCTAGAGTCGACGCGGCCGCGGAATTAACCCTCACTAAAGGGAACGAAT
                                        SalI
AAAAAAGCGAGCCATGGGCCCCTAGGAGATCTCAGCTGCGCCGGCGCCTTAATTGGGAGTGATTTCCCTTGCTTA

TCGGATCTACCTTCTGAAGACCAGAGAACCCCTGGGGAATTGCCCCGCCCTTTAAGGAAACCTCCTACACAGAGAGCTT
AGCCTAGATGGAAGACTTCTGGTCTCTTGGGGACCCCTTAACGGGGCGGGGAAATTCCTTTGGAGGATGTGTCTCTCGAA

TGGTAATTGTTCATGGTTTATACTTATCTCCAATAATGGATGTCATGGGGGGTTGAAAGTTTTGCATAACCGCTTTTTTT
ACCATTAACAAGTACCAAATATGAATAGAGGTTATTACCTACAGTACCCCCCAACTTTCAAAACGTATTGGCGAAAAAAA

TTTCTTCATGTTACCTGTCTTATTTAAAGGCAGGCCTACCTCAAAAACATTACACCAGTGGAGGAGAGAGAGAGAGAG
AAAGAAGTACAATGGACAGAATAAATTTCCGTCCGGATGGAGTTTTTGTAATGTGGTCACCTCCTCTCTCTCTCTCTC

AGAGAGAGAGAGAGAGAGAGAGAGAGAGAGTTACATTTGTTGAAAAAATAGTCATTTCATATCCTTTCCAGAAAGGAGAGGA
TCTCTCTCTCTCTCTCTCTCTCTCAATGTAAACAACTTTTTTATCAGTAAAGTATAGGAAAGGTCTTTCCTCTCCT

TGAAATTAGAAATGGACCCAGTTTTCAGTTTCTGATATCTTCAAAGTACCATCACCAAGAACAAGAACACTCAGACAAAA
ACTTTAATCTTTACCTGGGTCAAAAGTCAAAGACTATAGAAGTTTCATGGTAGTGGTTCTTGTTCTTGTGAGTCTGTTTT

ATCTAACCCAAACCCCATGCCTTCAAAGGGCATCTTCCACCTATGCGAAGGGCATGCCAAATTTTTAAGATTGGGAGTGA

TAGATTGGGTTTGGGGTACGGAAGTTTCCCGTAGAAGGTGGATACGCTTCCCGTACGGTTTAAAAATTCTAACCCTCACT

GGTGACATACAGGAAAAAATTTCTCTGTATTACCCAAAAAGAAAGTTTTGCTGGCAAGAATGATGTAAACAAAGCAAGGG
CCACTGTATGTCCTTTTTTAAAGAGACATAATGGGTTTTTCTTTCAAAACGACCGTTCTTACTACATTTGTTTCGTTCCC

CATTTTCTTTTCCTCCTTTTCTTTTTCTCCTTCCTTCCTTTCTTCCTTCCTTCCTTCCTTCCTTCCTTCCTTTCTTTCTT
GTAAAAGAAAAGGAGGAAAAGAAAAAGAGGAAGGAAGGAAAGAAGGAAGGAAGGAAGGAAGGAAGGAAGGAAAGAAAGAA

CTTTCTTTCTTTCTTTCTTTCTTTCTTTCTCCTGGGGNGGGGGTAGACTGCCAAACTAAGTATTTGTTTCTTGTAA
GAAAGAAAGAAAGAAAGAAAGAAAGAAAGAGGACCCCCCCCCATCTGACGGTTTGATTCATAAACAAAGAACATTT

| | |
|---|---|
| 5'-CGAATTCGGATCTACCTTCTGAAGACCAGAGAACCCCTGGGGAATTGCCC | (I) |
| 5'-CATGGTTTATACTTATCTCCAATAATGGATGTCATGGGGGGTTGAAAGTT | (II) |
| 5'-AGTCATTTCATATCCTTTCCAGAAAGGAGAGGATGAAATTAGAAATGGAC | (III) |
| 5'-TCAGACAAAAATCTAACCCAAACCCCATGCCTTCAAAGGGCATCTTCCAC | (IV) |

Fig. 4B

PARTICLE ANALYSIS ASSAY FOR BIOMOLECULAR QUANTIFICATION

1. RELATED APPLICATIONS

This application is related to and claims the benefit of U.S. Provisional Application Ser. No. 60/158,664 of Tore Straume, filed Oct. 8, 1999 and entitled "Multistep and Multiplex Separation of Nucleic Acids, Cells, and Other Objects," which is incorporated herein by this reference.

2. FIELD OF THE INVENTION

The present invention relates to methods for isolation, separation, and detection of selected objects. More particularly, the invention relates to methods for performing separations of objects, such as, without limitation, nucleic acids, proteins, cells, organelles, and the like.

3. TECHNICAL BACKGROUND

Separations of biological objects, such as proteins, chromosomes, nucleic acids, cells, organelles, and the like, and other types of objects are important in various detection, isolation, quantification, and diagnostic processes. Specificity and sensitivity are two important parameters that are generally desired in these separation schemes.

Hybridization probes are widely used to detect and/or quantify the presence of a particular nucleotide sequence in a mixed sample of nucleotide sequences. Hybridization probes detect the presence of a particular nucleotide sequence, referred to herein as a target sequence, through the use of a complementary nucleotide sequence that selectively hybridizes to the target nucleotide sequence. For a hybridization probe to hybridize to a target sequence, the hybridization probe must contain a nucleotide sequence that is complementary to the target sequence. The complementary sequence must also be sufficiently long for the probe to exhibit selectivity for the target sequence over non-target sequences.

Hybridization assays can be designed to detect the presence or absence of a particular nucleotide sequence, for example the presence of a gene in a DNA sequence. Hybridization assays can also be designed to detect the movement of a nucleotide sequence relative to another nucleotide sequence in a sample, for example the presence of a gene on a chromosome that is known to be normally located on a different chromosome, e.g., the detection of the abl gene on chromosome 22 in human leukemia patients (e.g., Tkachuk et al., 250 Science 559–562 (1990); C-TRAK translocation detection system commercially available from Oncor, Inc., Gaithersburg, Md.; U.S. Pat. No. 5,447,841; U.S. Pat. No. 5,731,153; and U.S. Pat. No. 5,783,387).

As used herein, "nucleotide sequence aberrations" refers to rearrangements between and within nucleic acids, particularly chromosomal rearrangements. "Nucleotide sequence aberrations" also refers to the deletion of a nucleotide sequence, particularly chromosome deletions. As used herein, the term "nucleic acids" refers to both DNA and RNA.

A chromosome translocation is an example of a nucleotide sequence aberration. A chromosome translocation refers to the movement of a portion of one chromosome to another chromosome (inter-chromosome rearrangement), as well as the movement of a portion of a chromosome to a different location on that chromosome (intra-chromosome rearrangement). In general, chromosome translocations are characterized by the presence of a DNA sequence on a particular chromosome that is known to be native to a different chromosome or different portion of the same chromosome. Because chromosome translocations involve the movement of a nucleotide sequence within a sample, as opposed to the appearance or disappearance of the nucleotide sequence, it generally is not possible to detect a chromosome translocation merely by assaying for the presence or absence of a particular nucleotide sequence.

Chromosome translocations are known to increase in frequency upon exposure to radiation and certain chemicals. Measurement of the frequency of chromosome translocations after exposure to radiation or a particular agent is therefore useful for evaluating the tendency of such agents to cause or increase the frequency of chromosome translocations. Also, the frequency (translocations per cell) of chromosome translocations measured in blood lymphocytes from an individual can be used as a quantitative measure of the amount of prior exposure to such agents (e.g., T. Straume and J. Lucas "Validation studies for monitoring of workers using molecular cytogenetics," Biomarkers in Occupational Health: Progress and Perspectives (M. L. Mendelsohn, J. P. Peeters, and M. J. Normandt, Eds.), Joseph Henry Press, Washington D.C., pp. 174–193 (1995)).

Chromosome translocations are also known to be associated with specific diseases, including, for example lymphomas and leukemia, such as Burkitt's lymphoma, chronic myelocytic leukemia, chronic lymphocytic leukemia, and granulocytic leukemia, as well as solid tumors such as malignant melanoma, prostate cancer, and cervical cancer. A method for efficiently detecting a translocation associated with a disease is needed as a method for diagnosing disease, follow-up of cancer therapy patients, research, and population studies.

Fluorescence in situ hybridization (FISH) using chromosome-specific composite hybridization probes ("chromosome painting") was developed as an assay for detecting chromosome translocations. FISH and selected applications of the FISH method are described in Pinkel et al., 83 Proc. Nat'l Acad. Sci. USA 2934–2938 (1986); Straume et al., UCRL 93837 (1986); Pinkel et al., 85 Proc. Nat'l Acad. Sci. USA 9138–9142 (1988); U.S. Pat. No. 5,447,841; Lucas et al., 62 International Journal of Radiation Biology 53–63 (1992); Straume et al., 62 Health Physics 122–130 (1992); Straume and Lucas, 64 Int. J. Radiat. Biol. 185–187 (1993).

The fluorescent hybridization probes used in FISH-based chromosome painting are substantially chromosome-specific, i.e., they hybridize primarily to a particular chromosome type. Unique or substantially unique probes may be used to limit non-specific hybridization. A discussion of so-called unique, middle repetitive, and highly repetitive sequences and their implications for hybridization probes is found in U.S. Pat. No. 5,447,841. Chromosome translocations are identified in the FISH assay by visually scanning individual cells for the presence of two different fluorescent signals on a single chromosome, the two fluorescent signals originating from two different cocktails of FISH probes, each probe cocktail having homology to a different chromosome type.

Because each FISH probe hybridizes to a specific chromosome type and not to the chromosome translocation itself, it is not possible to determine the frequency of chromosome translocations directly from the fluorescence signal emanating from a FISH probe. Rather, the frequency of chromosome translocations in a cell sample must be determined according to FISH assays by visually scanning individual metaphase cells on slides and identifying whether the two fluorescent signals appear on the same chromosome. The need to visually scan such individual cells effectively limits the number of cells that can be assayed, thereby reducing the sensitivity of the FISH assay, introducing the possibility of human error, and greatly increasing cost per analysis.

Accordingly, a fast, accurate method is needed for quantifying chromosome translocations and other nucleotide sequence aberrations. In particular, a method is needed that can isolate and quantify nucleotide sequence aberrations contained in the nucleic acid of a sample of cells without the need to analyze each cell individually.

U.S. Pat. No. 5,731,153 relates to a two-step separation procedure that uses two solid supports, each coated with unique complexing agents that bind to hybridization probes complementary to different target sequences. This procedure requires detachment of the target sequence from the first solid support after the first separation step and reattachment of the target sequence to a second solid support before the second separation step can be performed. The requirement for re-attachment of the target sequence is particularly problematic and would add significantly to the complexity and cost of commercial separation kits using such methodology and reduce the precision of the assay because of variability in the detachment/reattachment step. Further, this procedure is limited to two types of solid supports, but it would be useful to have more support options to facilitate multiple simultaneous analyses. Moreover, the preferable methods for quantification described in U.S. Pat. No. 5,731,153 require either very expensive and uncommon equipment (e.g., measure $^{14}$C by accelerator mass spectrometry) or much less quantitative methods such as the detection of fluorescence labels on reporter nucleic acid probes. Also, the method in U.S. Pat. No. 5,731,153 is limited to separation of nucleic acids, whereas it would be advantageous to separate other types of objects as well.

Unfortunately, methods available for the quantification of chromosomal rearrangements are either very costly and inefficient, e.g., cytogenetic-type analyses (H. J. Evans et al., 35 Chromosoma 310–325 (1971); D. Pinkel et al., 83 Proc. Natl. Acad. Sci. USA 2934–2938 (1986); D. Pinkel et al., 85 Proc. Natl. Acad. Sci. USA 9138–9142 (1988); D. C. Tkachuk et al., 250 Science 559–562 (1990)), or require small sequences such as fusion mRNAs that may be amplified by PCR and detected (M. H. Delfau et al., 4 Leukemia 1–5 (1990); A. Zippelius & K. Pantel, 906 Annals NY Acad. Sci. 110–123 (2000)). Cytogenetics require a highly trained technician to visually score metaphase or interphase cells using a microscope and make judgements about what is observed. PCR is less labor intensive than cytogenetics but is of limited utility in direct DNA-based detection of most chromosomal translocations because the fusion points tend to be variable. D. C. Tkachuk et al., 250 Science 559–562 (1990); E. Solomon et al., 254 Science 1153–1160 (1991). These limitations have essentially restricted PCR to the detection of fusion mRNAs, which may not always be known, may arise from ectopic expression, or may be expressed deficiently (A. Zippelius & K. Pantel, 906 Annals NY Acad. Sci. 110–123 (2000)).

In view of the foregoing, it will be appreciated that providing a separation method that does not require reattachment of the target sequence to a solid support to perform the second step, does not require PCR, is highly quantitative, can be accomplished using readily available laboratory equipment, can be used for multiple simultaneous analyses, and that is applicable to the isolation and quantitation of many different kinds of objects, including nucleic acids, metaphase chromosomes, proteins, cells, organelles, and the like, would be a significant advancement in the art.

Such methods are disclosed herein.

4. BRIEF SUMMARY OF THE INVENTION

The present invention provides methods for separation and quantitation of objects, including nucleic acids, chromosomes, proteins, organelles, cells, and the like.

In one preferred embodiment, the present invention relates to a method for separating nucleotide sequence aberrations from normal nucleotide sequences and quantification of the frequency of abnormal sequences. As used herein, "nucleotide sequence aberration" refers to rearrangements between and within nucleotide sequences, particularly chromosomes. "Nucleotide sequence aberration" also refers to the deletion of a nucleotide sequence, particularly chromosome deletions. As used herein, the term "nucleic acids" refers to both DNA and RNA of any origin and any level of organization, e.g., DNA, chromatin, and chromosome.

A method is provided for separating and quantifying nucleic acids that include a nucleotide sequence aberration, the nucleotide sequence aberration being identified by the presence of nucleotide sequences that include a first, a second, and additional ones if desired, nucleotide sequence types.

According to a preferred embodiment of the present invention, a nucleotide sequence aberration is isolated by separation of nucleic acids having both a first nucleotide sequence type (e.g., from a first chromosome) and a second nucleotide sequence type (e.g., from a second chromosome) from nucleic acid sequences not having both first and second sequence types. The presence of the first and the second nucleotide sequence types on the same nucleic acid indicate the presence of a nucleotide sequence aberration. Thus, nucleic acids that contain a nucleotide sequence aberration, characterized by their having nucleic acid sequences of both a first and a second nucleic acid sequence type, are selectively isolated. Once isolated, these sequences may be detected, quantified, and/or characterized.

In an illustrative embodiment of the invention, a target nucleic acid is isolated from a mixture of nucleic acids in a sample by hybridizing two or more hybridization probes to the mixture of nucleic acids, each probe type being specific for non-overlapping sequences on the target nucleic acid and containing complexing agents specific for selected types of solid support surfaces. Preferred embodiments include two different types of supports, one for separation (e.g., superparamagnetic microbeads or the inside surface of microtiter wells) and another for detection and quantification (e.g., magnetically non-responsive polystyrene microspheres of selected diameters that can be identified and counted in a particle size distribution analysis system such as a Coulter counter). For example, the first complexing agent on the first hybridization probe is contacted with the second complexing agent bound to a first bead that is responsive to a magnetic field (M) either before, during, or after the first and/or second hybridization probe is hybridized to the sample of nucleic acids. By contacting the first and second complexing agents, the first hybridization probe becomes immobilized on the magnetically responsive bead. This enables the immobilization of any nucleic acid hybridized to the first hybridization probe, i.e., a nucleic acid that includes a nucleic acid sequence of the first type. The magnetically responsive bead enables nucleic acids hybridized to the first hybridization probe to be separated from nucleic acids that do not hybridize to the first hybridization probe.

Similarly, the third complexing agent on the second hybridization probe is contacted with the fourth complexing agent bound to a second bead, which is non-responsive to a magnetic field (NM) but may be of different size than the first bead (and/or responsive to an electric field), either before, during, or after the first and/or second hybridization probe is hybridized to the sample of nucleic acids. By contacting the third and fourth complexing agents, the second hybridization probe becomes immobilized on the non-magnetic responsive bead. This enables the immobilization of any nucleic acid sequence hybridized to the second hybridization probe, i.e., a nucleic acid sequence that includes a nucleic acid sequence of the second type. The magnetically non-responsive bead can then be used as a detectable marker following magnetic separation for those target nucleic acids that have both type 1 and type 2 sequences on the same contiguous molecule. If the magnetically non-responsive bead is responsive to an electric field (e.g., by coating with carboxylic acid) and uniqely complexable to a solid support, two additional separation steps would be possible. For example, Step 1 could be by magnetic separation, Step 2 by electrophoretic separation, and Step 3 by complexing the non-magnetic beads to a solid support such as a glass slide and detection by fluorescence scanning, or to a solid support such as the inside surface of a well in a 96 well plate. Also, step 2 separation can be accomplished by filtration if different size beads are used, or by particle size characterization if a particle size measurement device is employed (these methods are taught in Example 2).

Only nucleic acids containing the first nucleic acid sequence type, i.e., nucleic acids that hybridize to the first hybridization probe, will be immobilized onto the magnetically responsive bead. Of these nucleic acids, only those containing the second nucleic acid sequence type will hybridize to the second hybridization probe, which is immobilized onto the magnetically non responsive bead. Thus, after the first separation step by response to magnetic force, followed by washing, the remaining target nucleic acids contain sequences hybridized to the first probe and sequences hybridized to both the first probe and the second probe. All target nucleic acid sequences not hybridized to the first probe, or not hybridized to the same contiguous nucleic acid molecule as the first probe, are washed out because they are not immobilized to the magnetic bead.

The aberrant nucleic acids, which contain sequences hybridized to the first probe and second probe, can be separated by exposure to an electric field if the second bead is responsive to an electric field, or by immobilizing the second bead to a solid support if the second bead is coated with a member of a third pair of complexing agents which is capable of specifically complexing with the complementary member of the third pair of complexing agents coated on the solid support. The detection and quantification of nucleic acids containing both type 1 and type 2 sequences, which is directly proportional to the number of nucleic acid aberrations present in the sample of nucleic acids analyzed, can be done using a variety of available methods. For example, various detectable labels can be included on the beads, on the probes, or on the target nucleic acid, such that they can be measured by fluorescence, radioactivity, luminescence, chemiluminescence, electrochemiluminescence, spectrophotometry, and the like. Colored beads, both fluorescent and non-fluorescent, are commercially available (e.g., Bangs Labs, Fishers, Ind.) and also can be used for distinguishing nucleic acid types.

The method of the present invention increases by orders of magnitude the speed of detecting nucleotide sequence aberrations, such as chromosome translocations, over current detection methods, including FISH assays.

Since the number of type 1 plus type 2 target sequences detected in the sample of DNA analyzed would be proportional to the number of type 1 plus type 2 nucleotide sequences in the cell extract (e.g., chromosomal DNA from blood lymphocytes), the method of the present invention can also be used in the early detection and monitoring of pre-clinical disease progression of malignancies, such as leukemias that are associated with specific chromosomal rearrangements, e.g., t(9;22) of human chronic myelogenous leukemia. According to this embodiment of the method, the first and second hybridization probes are designed to selectively hybridize to a first and a second nucleic acid sequence types, the nucleotide sequence aberration of which is associated with and/or characteristic of a disease. Only nucleic acids containing both the first and second nucleotide sequence types, the aberration of which is associated with and/or characteristic of a disease, will hybridize to both the first and second hybridization probes. As a result, after the first separation by magnetic force followed by washing, the separation of the beads complexed to the second hybridization probe, either by electric force, immobilization on a solid support, bead filtration, or particle size analysis, may be used to diagnose a disease associated with the particular nucleic acid aberration being detected. Examples of diseases that may be detected include (but are not limited to) cancers such as leukemia, lymphoma, melanoma, prostate, and cervical cancer.

It is within the scope of the present invention that probe-bead attachments and hybridizations of probes to target nucleotide sequences can be performed in any order, as well as simultaneously.

In another preferred embodiment of the invention, the present method can be used for separating and rapidly quantifying objects such as proteins, cells, organelles, and the like. Instead of using hybridization probes for binding to the target object, antibodies or other binding molecules, such as lectins, are used. It is merely required that there be at least two binding sites on the target for which there is a corresponding number of binding molecules. For example, a protein having two epitopes can be separated from other proteins provided that an antibody for binding each epitope is available for carrying out the separation. Example 4 teaches the separation of cells using the methods of the present invention.

In another preferred embodiment of the invention, beads of different sizes can be used for carrying out separation steps. For example, if a small magnetically non-responsive bead is coupled to an antibody that recognizes one epitope and a larger magnetically responsive bead is coupled to an antibody that recognizes another epitope, then nucleic acids, proteins, cells, organelles, and the like that bear both epitopes can be separated from other objects that lack both epitopes. A description of this embodiment of the invention is provided in Example 2 for nucleic acids, Example 4 for cells, and Example 7 for proteins.

It will be recognized by those skilled in the art that at least the following differences among beads can be used for carrying out multi-step separations: the degree of magnetic responsiveness, the degree of charge responsiveness, selected bead size differences, selected bead color differences, and selected complexing agents on beads and supports.

The present invention also relates to a kit for separating and quantifying nucleic acid aberrations and diagnosing disease according to the methods of the present invention. In general, the kits of the present invention include beads with complexing agents and hybridization probes (e.g., magnetically responsive beads coated with type 1 probes and magnetically non-responsive beads coated with type 2 probes). The kits may also include vials with reagents, suitable solid supports, instructions for using the kit, and a calibration curve (or suitable internal control) relating the measured quantity to the frequency of nucleic acid sequence aberrations in the target sample.

5. BRIEF DESCRIPTION OF THE SEVERAL VIEWS OF THE DRAWINGS

FIGS. 1A, 1B, 2A, and 2B show exemplary methods for separating and isolating a chromosome translocation. FIG. 1 shows the isolation of DNA from a sample of cells, hybridization of the DNA to first and second hybridization probes, attaching the hybridized DNA to a first bead that is magnetically responsive and specifically complexes with the first hybridization probe and a second bead that is magnetically non-responsive and specifically complexes with the second hybridization probe, and a first separation step accomplished by subjecting the mixture of bead-attached hybridized DNA to a magnetic force followed by washing. At this stage, the beads can could be detached from the target DNA (e.g., by DNase treatment) and directly analyzed as described in Example 6. FIG. 1B depicts a similar procedure in which the probes are attached to a non-magnetic solid support such as the inside surface of a well of a microtiter plate, permitting step 1 separation followed by bead counting or particle size distribution analysis. FIG. 2A depicts the second separation step of DNA that contains both type 1 and type 2 sequences from a sample of cells, wherein the second bead is magnetically non-responsive but is electrically responsive, after the first step separation, the DNA containing both type 1 and type 2 sequences is then separated by application of an electric force. FIG. 2B shows the second separation step of DNA that contains both type 1 and type 2 sequences from a sample of cells, wherein the second bead is capable of specifically complexing with the second hybridization probe and a solid support, after the first separation step, the DNA containing both type 1 and type 2 sequences is separated by complexing the second bead to a solid support, followed by washing.

FIGS. 3A–B illustrate a pUC 19 plasmid and a 18.2 kb DNA insert used here as a model system to demonstrate the feasibility of the separation method presented in this invention.

FIG. 4 shows the sequences of the terminal ends (SEQ ID NO:1 and SEQ ID NO:2) of the DNA insert seen in FIG. 3B and the 50mer probes (SEQ ID NOS:3–10) selected to be complementary for type 1 (one of the ends) and type 2 DNA (the other end).

Figure 7:
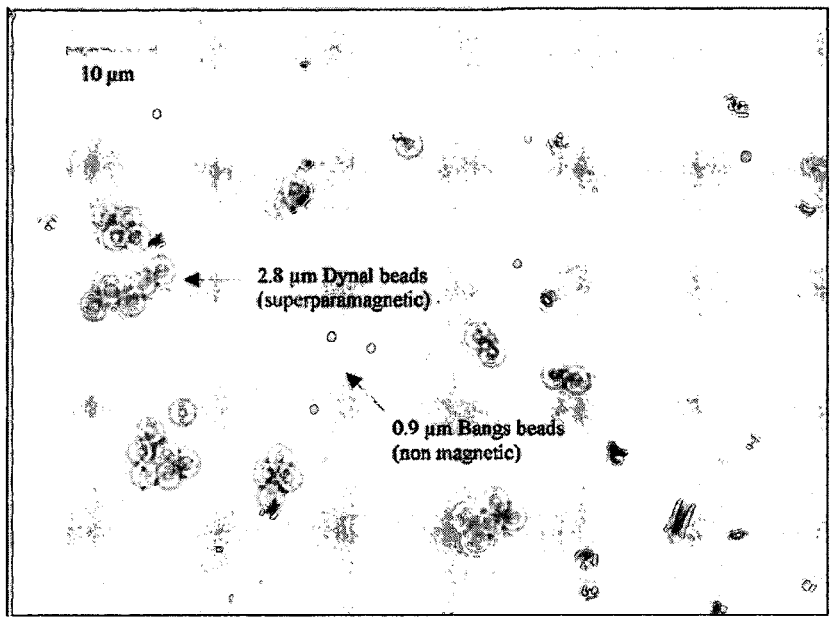

FIG. 7 shows a microscope image following hybridization of beads to the 18.2 kb target DNA and magnetic separation. In this case, 1 µl of Solution B was deposited on a slide and HA on the Bangs beads complexed with the anti-HA on the surface of the slide. After washing, only the Bangs beads attached to the slide. The Dynal beads, which were connected to the Bangs beads because they were both hybridized to the same DNA molecule, are also present on the slide. The presence of both Dynal and Bangs beads on this slide demonstrates that both were hybridized to the target DNA and that the separation procedure was successful.

Figure 8:
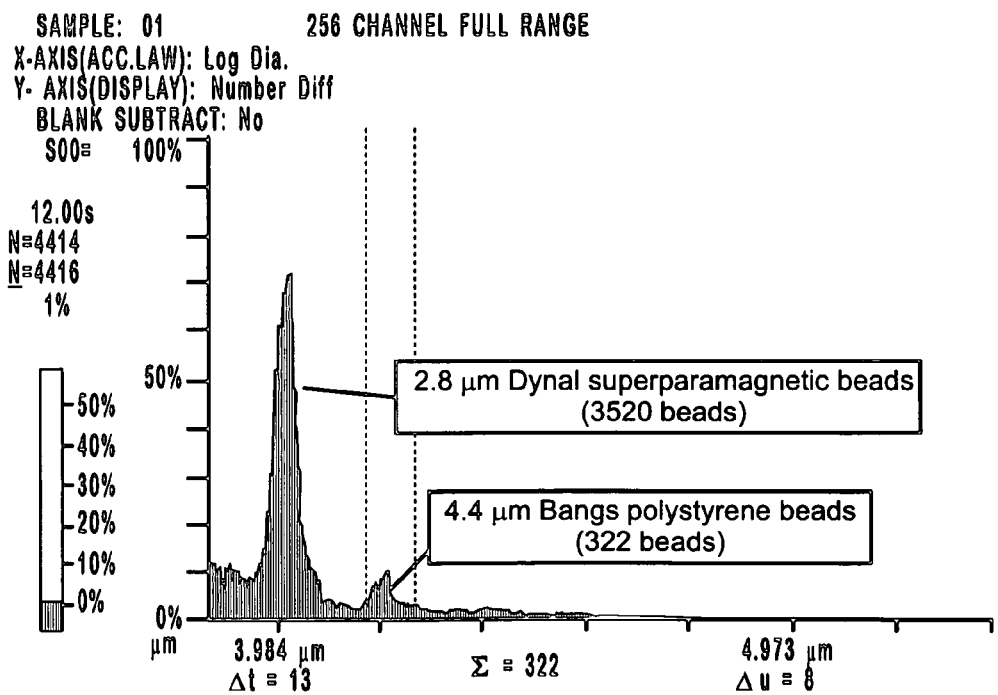

FIG. 8 illustrates the particle size distribution obtained for the two bead types following magnetic separation of the 18.2 kb target DNA sequence. In contrast with the results in Table 1, in this case, the larger non-magnetic beads were selected to place the non-magnetic bead peak in a region of lower background counts. The materials and methods used to obtain these results were the same as those used for Table 1 with the following differences: FIG. 8 used 4.4 µm diameter magnetically non-responsive polystyrene beads coated with streptavidin (Bangs Labs, Fisher, Ind.) whereas Table 1 used 0.94 µm diameter magnetically non-responsive polystyrene beads coated with streptavidin (Bangs Labs); FIG. 8 used 5 µg of 18.2 kb target DNA whereas Table 1 used 20 µg of 18.2 kb target DNA; partial magnetic separation was done for FIG. 8 following DNase treatment to reduce (but not fully eliminate) the number of superparamagnetic beads to provide a lower background level while at the same time provide a 2.8 µm peak for comparison/illustration purposes; and for FIG. 8 the final bead concentration was diluted two-fold just before generating the bead size distributions using the Coulter Multisizer II. It is clear that separation and quantification of these bead types can be accomplished using our methods and commercially available particle analyzers.

Figure 9:
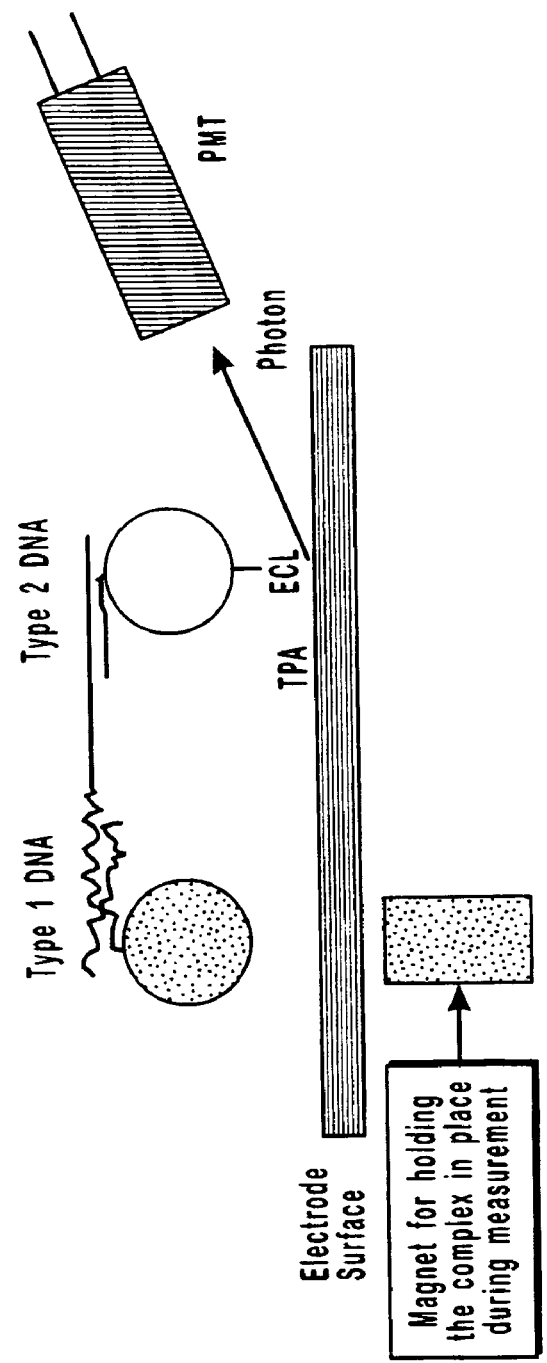

FIG. 9 illustrates Type 1 and Type 2 DNA and the beads with ECL labels and probes for detection of the non-magnetic beads by electrochemiluminescence (ECL). Note that the hybridization could occur in any order, prior to, during, or after complexing the probes with the beads. If attachment of probes to the beads is performed first in separate solutions, then both bead types can use the same complexing agents (e.g., avidin-biotin). However, if the probes are hybridized first (which is the preferred method) then the complexing agents binding the beads to the respective probes would be unique and specific for each bead-probe complex. In this case, we could use streptavidin coated magnetic beads that would complex with biotinylated probes and antidigoxigenin coated non-magnetic beads that would complex with digoxigenin labeled probes. As depicted, a magnet may be used to hold the complex in place during measurement.

Figure 10:
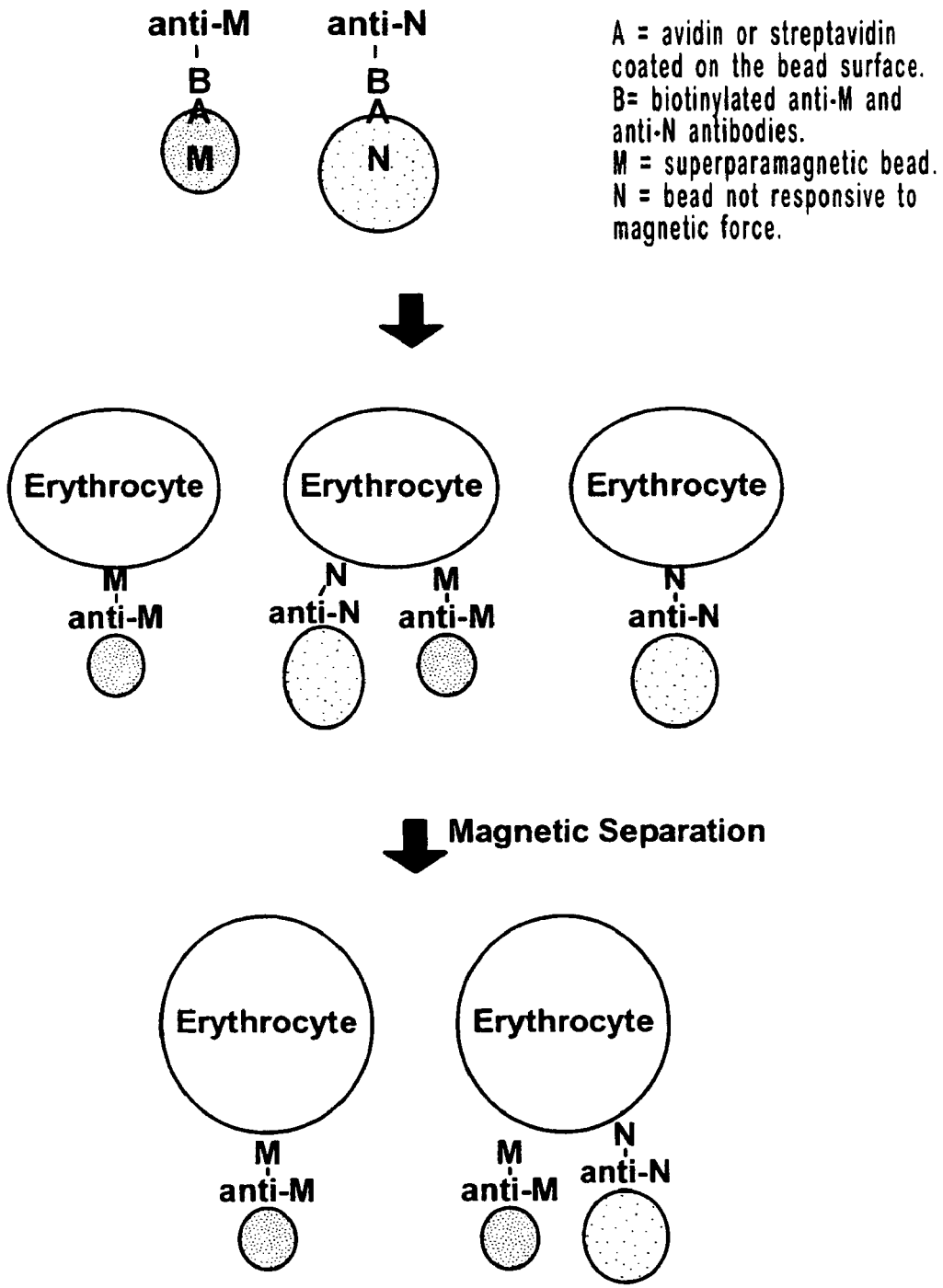

FIG. 10 shows the separation of erythrocytes containing the glycophorin MN surface proteins from all other erythrocytes.

Figure 11:
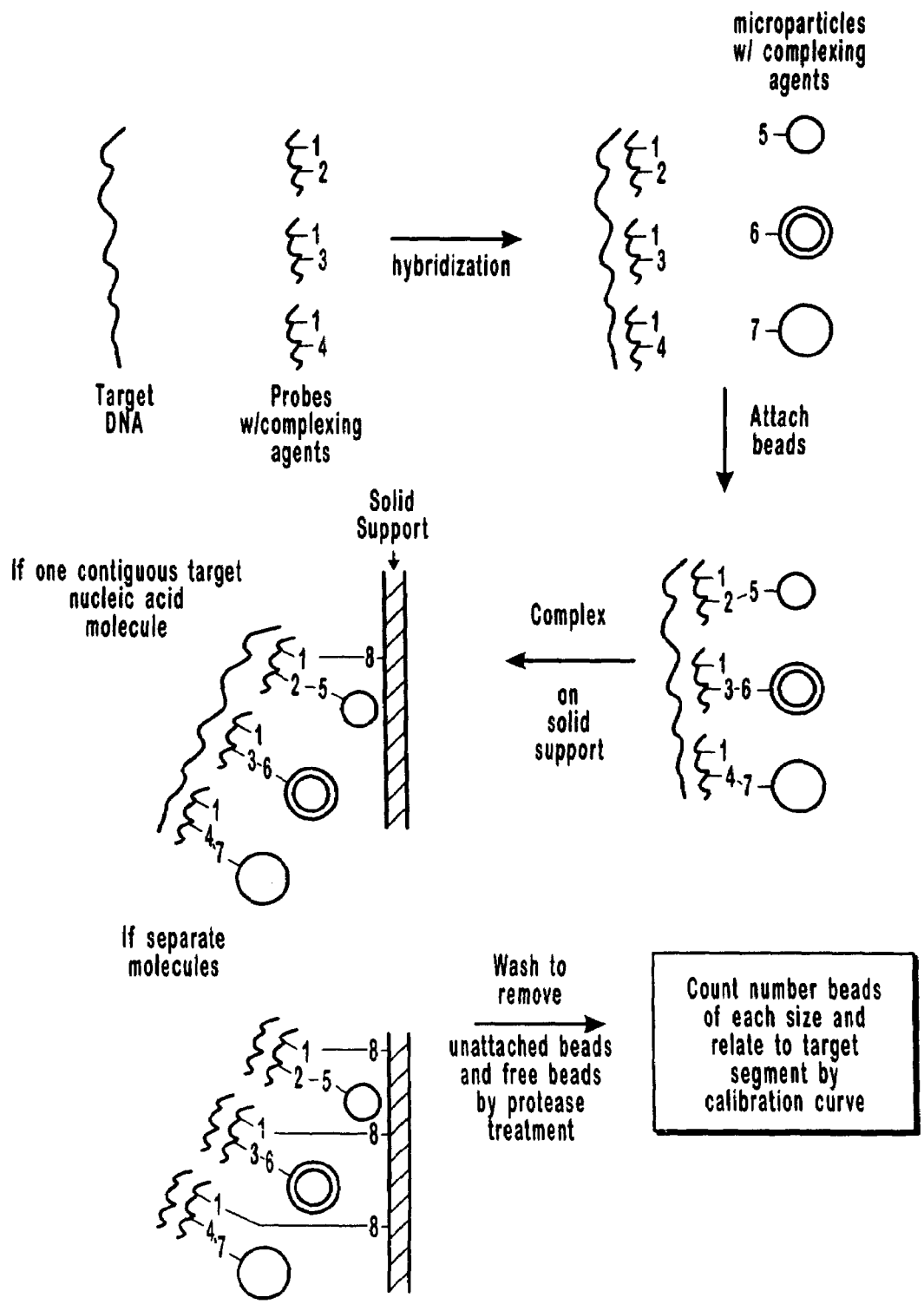

FIG. 11 illustrates a method for evaluating for the presence, absence, or amplification of nucleic acid sequences in a sample of nucleic acid. The examples of complexing agents are as follows: 1=biotin; 2=digoxigenin; 3=estradiol; 4=fluoresceine; 5=antidigoxigenin; 6=anti-estradiol; 7=anti-fluoresceine; and 8=avidin.

FIGS. 12A–D illustrate particle size spectra obtained using the particle counting assay to detect bcr/abl fusions in genomic DNA isolated from human CML cells. FIGS. 12A–C are the spectra of microparticles observed in 500 µl samples with 165 ng, 16.5 ng, and 0 ng of genomic K-562

DNA, respectively. FIG. 12D is the result obtained with 16.5 ng genomic K-562 DNA when the probes were not present during hybridization.

Figure 13:
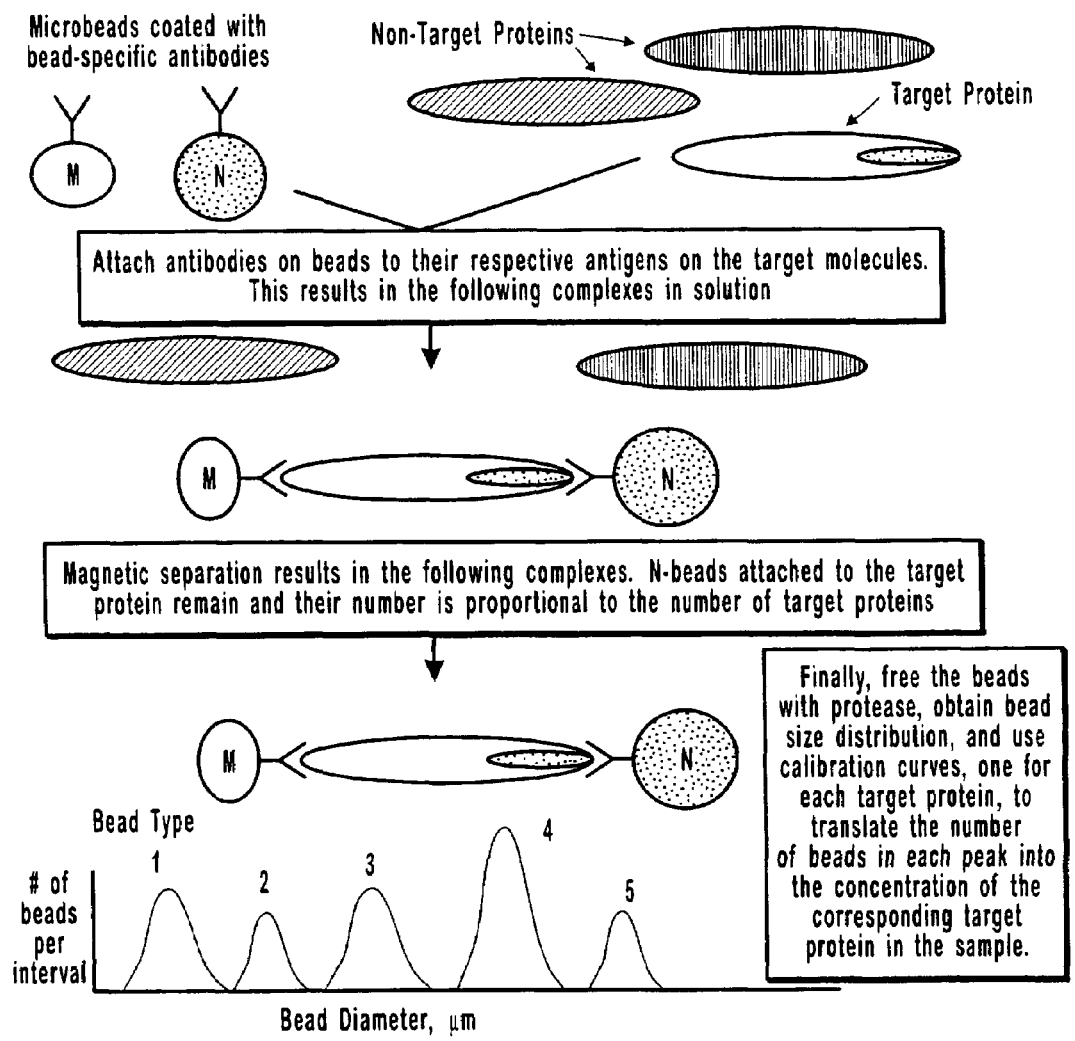

FIG. 13 illustrates a method to simultaneously separate and quantify selected target molecules (e.g., proteins) using antibodies and beads of different diameters. Magnetic (M) beads and non-magnetic (N) beads are complexed with selected antibodies that permit their unique attachment to different antigenic sites on the same target molecule. Note that the N-beads will remain after magnetic separation only if both antigenic sites are present on the same contiguous molecule.

Figure 14:
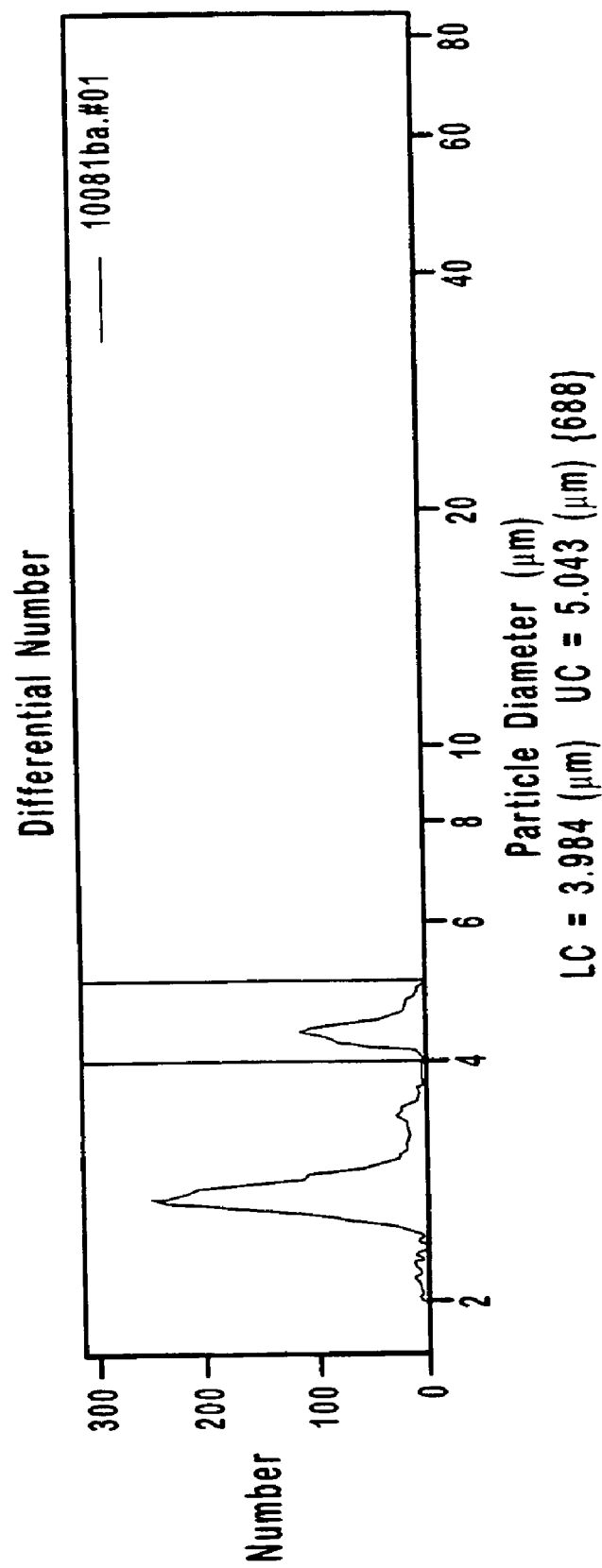

FIG. 14 shows the particle size distribution obtained using the described method to separate ferritin.

Figure 15:
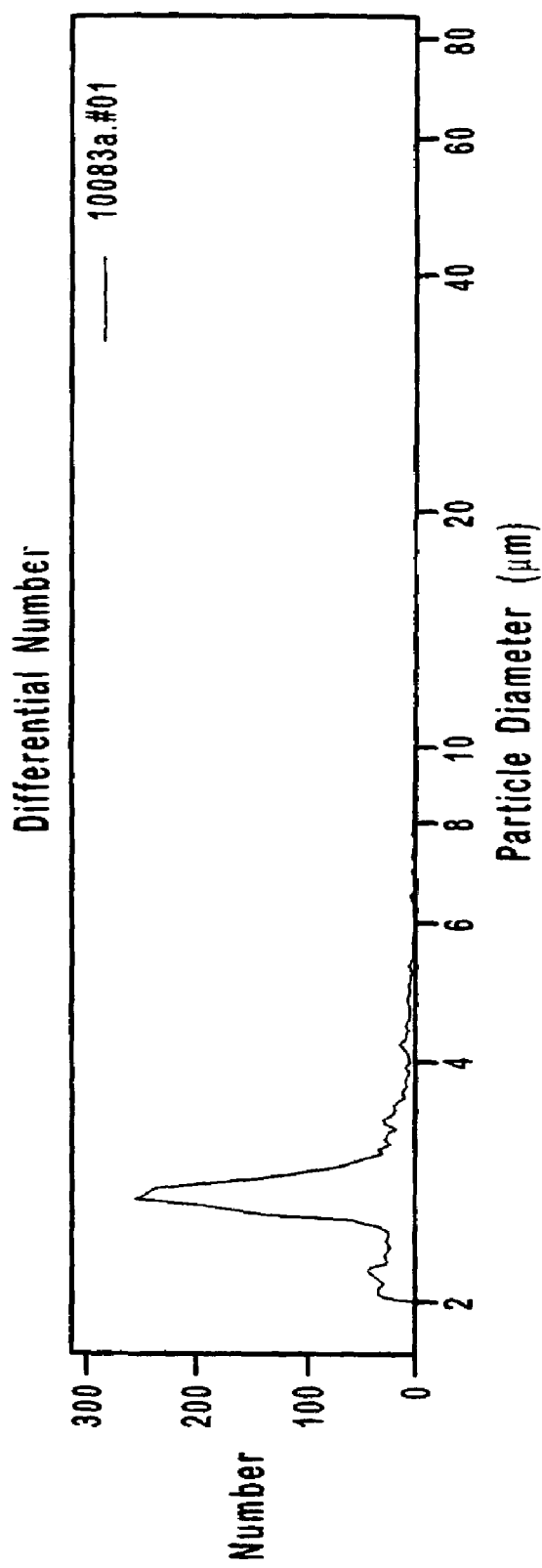

FIG. 15 shows the results obtained by repeating the separation in FIG. 14, but without ferritin in the target solution.

6. DETAILED DESCRIPTION

Before the present compositions and methods for separation and quantitation of aberrant nucleic acid sequences, other molecules, cells, and the like are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out herein.

In one illustrative embodiment, the present invention relates to a multi-step method for detecting and separating nucleic acid sequence aberrations. As used herein, the term "nucleotide sequence aberration" refers to rearrangements between and within nucleotide sequences, particularly chromosomes. Nucleotide sequence aberration also refers to the deletion of a nucleic acid sequence, particularly chromosome deletions. As used herein, the term "nucleic acids" refers to DNA and RNA of any origin, and any level of organization, e.g., DNA molecule, chromatin, chromosome.

According to the method of the present invention, a nucleotide sequence aberration is detected by isolating and quantifying nucleotide sequences having both a first nucleotide sequence type (e.g., from a first chromosome) and a second nucleotide sequence type (e.g., from a second chromosome). The presence of the first and the second nucleotide sequence types on the same nucleic acid indicating the presence of a nucleotide sequence aberration.

Figure 1A:
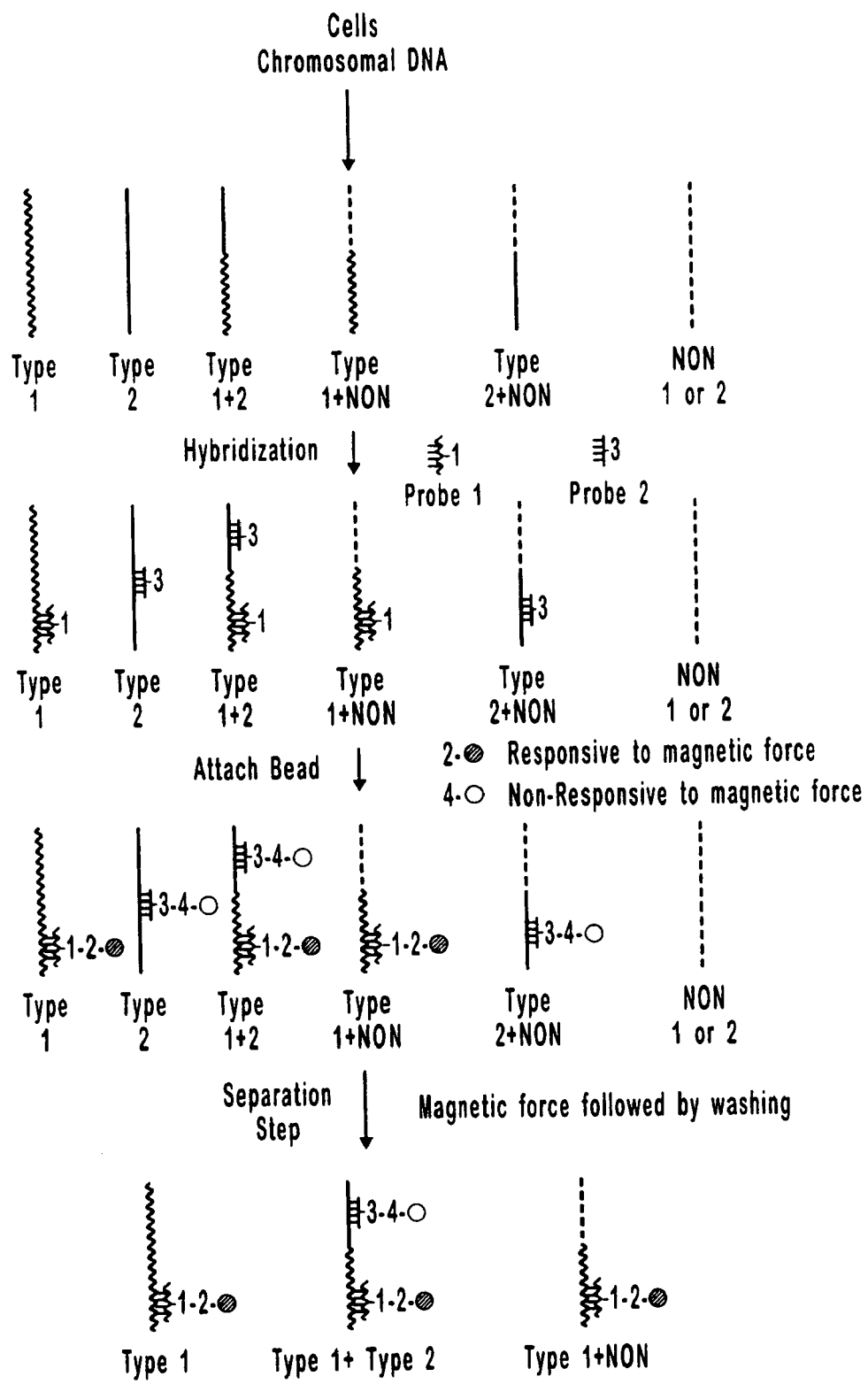
Figure 1B:
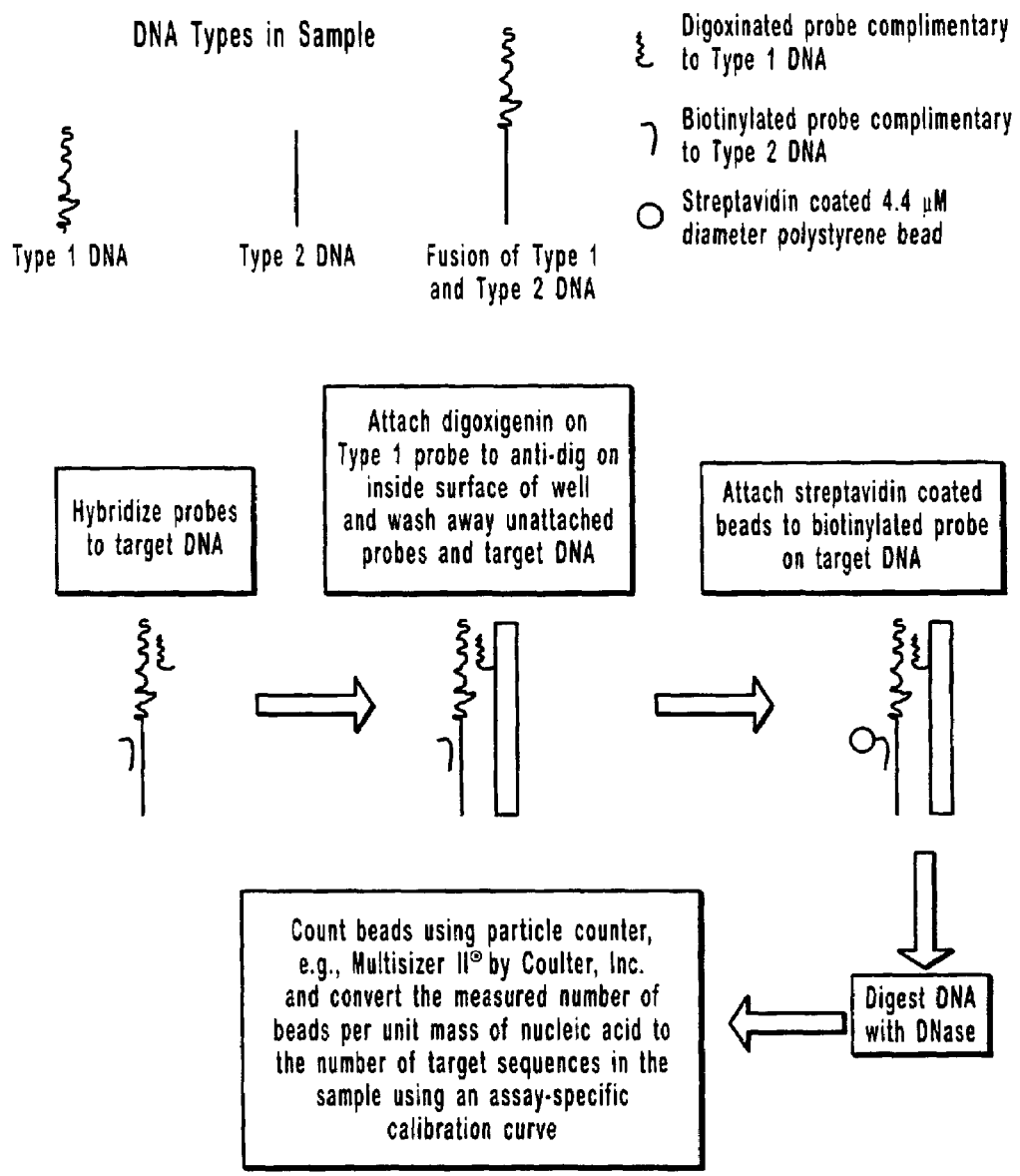

The method is referred to as a multi-step method because it involves at least two sequential separation steps. According to the method of the present invention, as illustrated in FIG. 1, the nucleic acid sample comprises chromosomal DNA isolated from a sample of cells. Chromosomal DNA may be isolated by any of the variety of methods known in the art. For example, the DNA may be isolated by the method taught in U.S. Pat. No. 5,477,841 and references therein; in Vooijs, et al,. Am. J. Hum. Genet. 52:586–597 (1993); or by using the GIBCO BRL TRIzol™ Reagent (Life Technologies, Gaithersburg, Md.), or by using a QIAprep kit (Qiagen, Inc., Valencia, Calif.).

Chromosomal DNA may be analyzed as whole chromosomes, chromosome fragments, chromatin fragments, or chromosomal DNA fragments, all of which are hereinafter referred to as chromosomal DNA. When analyzing chromosomal DNA for the presence of nucleotide sequence aberrations, the chromosomal DNA may be organized as an extended double strand, as extended nucleosomes, as chromatin fiber, as folded fiber, and as interphase, prophase, or metaphase DNA. Sandberg, "The chromosomes in human cancer and leukemia", Elsevier; N.Y. ( 1980), pp. 69–73.

The preferred chromosome organization for assaying chromosomal DNA for the presence of a nucleotide sequence aberration depends on the number of bases separating the first and second nucleotide sequence types being recognized by the first and second hybridization probes used to identify the aberration. The preferred size of beads is a function of the size of the piece of target DNA or RNA to be evaluated. For example, target pieces of DNA can range from less than a micrometer to several millimeters in length depending on the level of organization used and the degree to which the chromosomes are fractionated. For example, accurate quantification of the frequency of t(9;22) fusions in chronic myelogenous leukemia (CML) patients would require target DNA pieces on the order of a few hundred kilobases (less than 1 mm) if the DNA molecules are fully extended and only a few micrometers if the chromosomes are in the interphase level of organization. (Note that the position of the fusion point in CML patients can vary by about 225 kb.)

Although it is within the scope of the present invention that probe-bead attachments and hybridizations of probes to target nucleotide sequences can be performed in any order, as well as simultaneously, as illustrated in FIG. 1, it is an embodiment of this invention that the following order be used to reduce the number of complexing agents required (e.g., see Example 1). Two different probe-bead complexes are prepared in separate solutions. Solution I would contain the first hybridization probe with a member of a pair of first complexing agents capable of attaching to a complementary member of the first pair of complexing agents. Also contained in Solution I would be magnetically responsive beads coated with the complementary member of the pair of first complexing agents. The beads and hybridization probes would be combined in Solution I such that complexing of the pair of first complexing agents takes place. Subsequent washing would remove all probes and reagents not complexed with the beads. Solution II would contain the second hybridization probe with a member of a second pair of complexing agents capable of attaching to a complementary member of the second pair of complexing agents. Also contained in Solution II would be magnetically non-responsive beads coated with the complementary member of the second pair of complexing agents. The beads and hybridization probes would be combined in Solution II so as to permit complexing of the second pair of complexing agents. Subsequent washing would remove all probes and reagents not complexed with the beads. The magnetically non-responsive beads in Solution II may also be coated with a member of a third pair of complexing agent to facilitate a particular Step 2 separation embodiment, if desired (see below).

The two types of probe-bead complexes are then combined in one solution and contacted with a sample of target nucleic acid sequences under conditions favorable for hybridization. The first hybridization probe includes a nucleotide sequence probe that is at least partially complementary to a first target nucleotide sequence type. The second hybridization probe includes a nucleotide sequence that is at least partially complementary to a second nucleotide sequence type and that selectively hybridizes to the second nucleotide sequence type over the first nucleotide sequence type.

In the case of detecting and separating chromosomal translocations, the first hybridization probe is preferably a chromosome-specific probe such that it selectivity hybridizes to a particular chromosome type. In the case of detecting inter-chromosomal rearrangements, "chromosome type" refers to individual chromosomes. In the case of detecting intrachromosomal rearrangements, "chromosome type" refers to different portions of an individual chromosome since intra-chromosomal rearrangements involve the movement of a sequence to a different portion of the same chromosome.

Any hybridization probe that preferentially hybridizes to a particular nucleotide sequence may be used as the first hybridization probe and is intended to fall within the scope of the present invention. In the case of detecting chromosome translocations, a large number of both chromosome-specific painting probes and unique sequence probes are available commercially (e.g., Oncor, Inc., Gaithersburg, Md.; or Vysis, Inc. (www.vysis.com)). In addition, methods are broadly available for anyone skilled in the art to prepare nucleic acid probes that are complementary to any known sequence. For example, thousands of human genes have now been mapped to specific regions of chromosomes and sequenced. These sequences are now available on the Internet and can be used to make biotinylated type 1 and type 2 probes for use in the present invention to quantify DNA rearrangements (see Example 1). Exemplary methods for preparing DNA probes for chromosome translocation detection are given in U.S. Pat. No. 5,447,841, which is hereby incorporated herein by reference. A preferred modification to the method of U.S. Pat. No. 5,447,841 is the use of biotin TEG phosphoramidite to attach individual biotin molecules to the 5' end of the probes (see Example 1).

Because the first hybridization probe is selective for a first nucleotide sequence type as opposed to the nucleotide sequence aberration itself, the first hybridization probe hybridizes to all nucleotide sequences containing the first nucleotide sequence type. For example, with regard to detecting a chromosome translocation, the first hybridization probe may be a chromosome-specific probe. Thus, the first hybridization probe does not by itself detect the nucleotide sequence aberration. Rather, the method of the present invention relies on the second hybridization probe to identify those nucleotide sequences isolated by the first hybridization probe that also have a nucleotide sequence of a second type. By contrast, in most prior art hybridization assays using two hybridization probes, the first hybridization probe selectively isolates the nucleic acid being detected while the second hybridization probe serves to enable detection of the nucleotide sequence isolated by the first hybridization probe.

The first hybridization probe also includes a complexing agent that is configured for binding to a complementary complexing agent for forming a first pair of complexing agents. The complementary complexing agent is attached to a first bead, which is responsive to magnetic force, thereby enabling the immobilization of the first hybridization probe on the magnetically responsive bead. The second hybridization probe includes another complexing agent that is configured for binding to another complexing agent for forming a second pair of complexing agents. The complementary complexing agent of the second pair of complexing agents is attached to a second bead, which is non-responsive to magnetic force, but is either electrically responsive, is coated with a complexing agent that is configured for binding to still another complementary complexing agent for forming a third pair of complexing agents, and/or is of different size than the first bead. The complementary complexing agent of the third pair of complexing agents is attached to a solid support, thereby enabling the immobilization of the second hybridization probe on the solid support.

The first, second, and third pairs of complexing agents may be any pair of complexing agents that form a strong binding pair. Since elevated temperatures may be required for hybridization, the binding pair should preferably be stable at temperatures at least up to about 40° C.

Examples of suitable binding pairs of complexing agents include biotin-avidin, and antibody-antigen pairs, such as hemagglutinin and anti-hemagglutinin, and digoxigenin and anti-digoxigenin. Avidin-biotin and analogues and derivatives thereof are particularly preferred as binding pairs due to their enhanced thermal stability.

Magnetically responsive and magnetically non-responsive beads suitable for the present invention are commercially available (Dynal AS, Oslo, Norway; Bangs Labs, Fishers, Ind.). Preferably the first bead is magnetically responsive and the second bead is non-responsive to magnetic force, but is either responsive to electric force, coated with an additional complexing agent (e.g., a peptide for step 2 antibody separation), or smaller in size than the first bead, thus facilitating step 2 separation by filtration or by particle size distribution analysis (see Example 2). Preferably, both bead types are coated with avidin as a complexing agent for attachment to uni-labeled biotinylated probes (i.e., only one biotin per probe). The magnetically non-responsive beads may also be coated with, e.g., carboxylic acid, which provides a negative surface charge and which would make them responsive to electric force.

Any solid support to which a complexing agent may be attached may be used in the present invention. Examples of suitable solid support materials include, but are not limited to, silicates such as glass, plastics, polyethylene, cellulose and nitrocellulose, polymethacrylate, latex, rubber, fluorocarbon resins such as TEFLON, metals, nylon, polystyrene, and the like.

The solid support material may be used in a wide variety of shapes including, but not limited to microscope slides, microspheres, and microtiter wells. Examples are provided herein of attachments to glass microscope slides and quantification by fluorescence scanning or microscopy (Example 1), and also of the use of different bead sizes, filtering, and quantification by bead counting or size characterization (Example 2).

Preferably, avidin or an avidin derivative is used in both the first and second pairs of complexing agents. Magnetically responsive and magnetically non-responsive microbeads labeled with streptavidin may be obtained from Dynal AS, Oslo, Norway, or Bangs Labs, Fishers, Ind. (see Example 1).

The first and second hybridization probes may be immobilized to the first bead or second bead either before, during, or after the first and second hybridization probes are hybridized to the sample of target nucleic acids. The first and second hybridization probes are preferably attached to the beads in separate solutions before the probes are hybridized to the sample of nucleic acids. This permits the use of biotin-avidin complexing agents for both bead types. Note, in this case, only one biotin is attached to each probe such that after binding to the beads and washing there is no unbound biotin on the probes to permit cross reaction between the beads (see Example 1).

Once target nucleic acids have been hybridized to the first and second hybridization probes immobilized on the first and second beads, the nucleic acids that hybridized with the first hybridization probe may be isolated by subjecting the hybridization mixture to a magnetic force followed by washing. Any non-hybridized nucleic acids and nucleic acids not containing type 1 sequence, are washed out because they are not complexed with the magnetically responsive bead.

The second hybridization probe includes a nucleotide sequence that does not hybridize to nucleic acids of the same type as the first hybridization probe. Any nucleotide sequence that does not hybridize to the first target nucleotide sequence type may be used in the second hybridization probe and is intended to fall within the scope of the present invention. Both hybridization probes may include analytically detectable markers that could be used to quantify the frequency of the nucleotide sequence aberration being detected. Furthermore, both types of beads can be tagged with detectable markers using methods available to someone with ordinary skill in the art. Also, beads are now available commercially in a wide selection of colors, e.g., from Bangs Labs, Fishers, Ind.

Optionally, the second hybridization probe may hybridize to more than one chromosome type other than the chromosome type to which the first hybridization probe hybridizes, e.g., a heterogeneous mixture of unique sequences selected from many non-type 1 chromosomes (see U.S. Pat. No. 5,447,841). In this embodiment the second hybridization probe would permit the detection of a larger fraction of the nucleotide sequence aberrations involving the chromosome identified by the first hybridization probe.

Where possible, the hybridization probe preferably includes a nucleotide sequence that is uniquely specific to the nucleotide sequence aberration being detected. The use of uniquely specific hybridization sequences is preferred since it minimizes the occurrence of background noise due to nonspecific hybridization. It is also possible to use a composite second hybridization probe that includes a series of sequences that are all either unique or chromosome specific for the aberration being detected. Such a composite "cocktail" of probes, if each with detectable markers, would enhance the signal to be detected and thus potentially decrease the limit of detection for the assay.

Figure 2A:
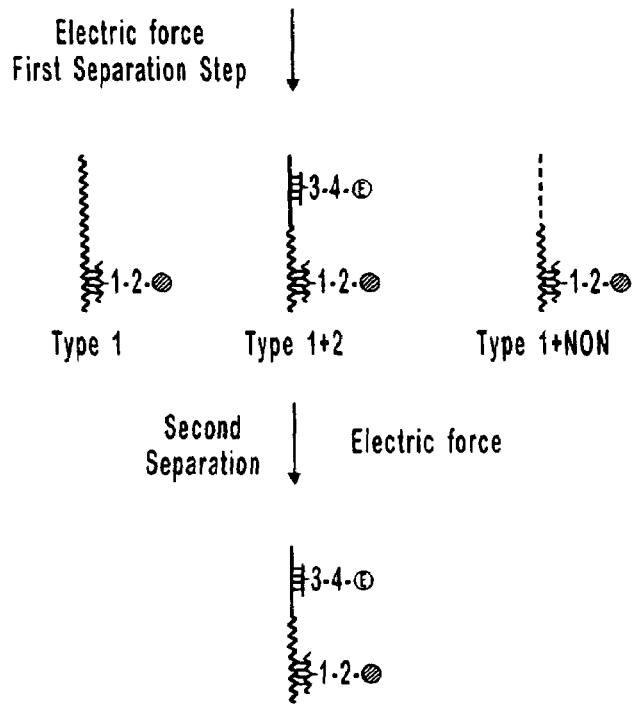
Figure 2B:
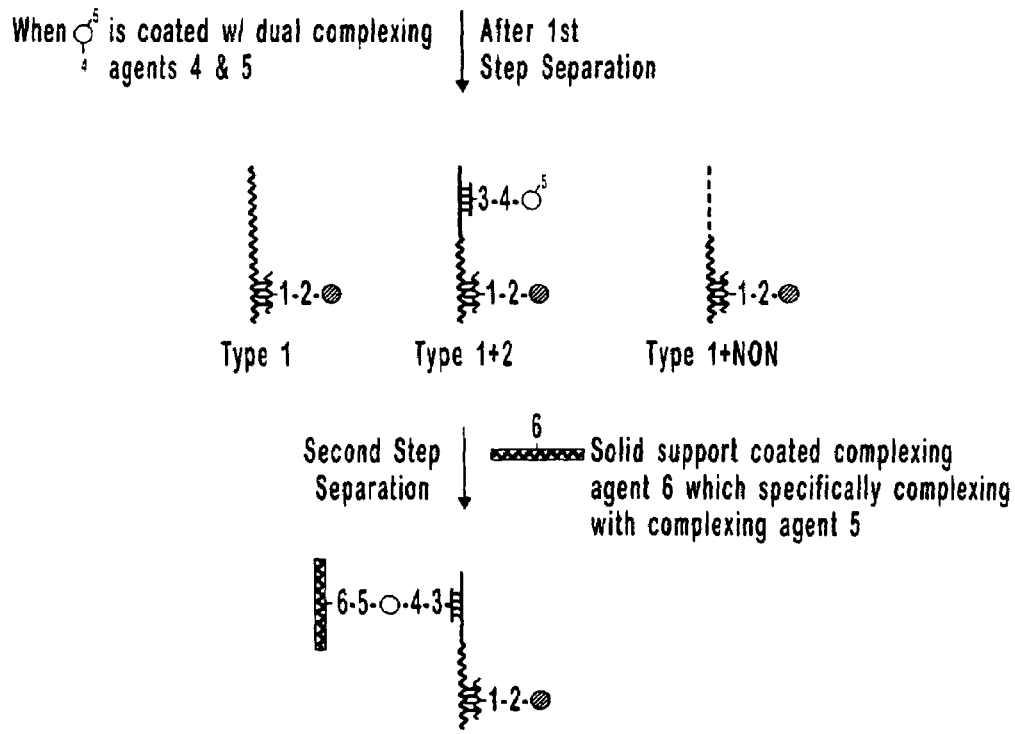

After the first step of magnetic force separation, the remaining target nucleic acids contain type 1 sequence complexed with the magnetic responsive beads, type 1+non complexed with magnetic responsive beads, or type 1+type 2 sequences if a rearrangement (fusion) between type 1 and type 2 nucleic acids has occurred (see FIG. 1). FIGS. 2A and 2B illustrate two embodiments of the second separation step of the present invention. According to FIG. 2A, the second bead used is non-responsive to magnetic force, but responsive to electric force. After hybridization and the first step of magnetic force separation described above, the nucleic acids that contain both type 1 and type 2 sequences can be separated by application of an electric force, because only nucleic acids containing both type 1 and type 2 can be complexed with the second bead, which is electrically responsive. It should be noted that since the nucleic acids containing both type 1 and type 2 sequences are responsive to both magnetic and electric forces, they can be purified through additional cycles of application of magnetic and electric forces.

According to FIG. 2B, the second bead used is non-responsive to magnetic force, but is coated with another complexing agent in addition to complexing agent from the second pair of complexing agents. This additional complexing agent is configured for forming a specific complex with a complementary complexing agent that is coated on a solid support. The combination of these two complexing agents forms a third pair of complexing agents. After hybridization and the first step of magnetic force separation described above, the nucleic acids containing both type 1 and type 2 sequences can be separated by immobilization on the solid support, because only nucleic acids containing both type 1 and type 2 can be complexed with the solid support by forming a complex between the third pair of complexing agents. After washing to remove unattached bead-DNA complexes, the immobilized nucleic acids containing type 1 and type 2 sequences may be detected by a variety of methods known in the art including, but not limited to, automated fluorescence scanning (e.g., tagged beads in a miniarray format), microscopy, etc. (see Example 1).

According to the method of the present invention, the first separation step enables the separation of nucleotide sequences of a first nucleotide sequence type. Since the second hybridization probe is designed so that it does not hybridize to nucleotide sequences of the first nucleic acid type, the second hybridization probe does not bind to nucleic acids immobilized by the first hybridization probe that do not contain a nucleotide sequence aberration. As a result, the number of target nucleic acid fragments (or metaphase chromosomes) that contain both type 1 and type 2 sequences isolated after the second step is proportional to the number of nucleotide sequence aberrations in the sample of nucleic acids being analyzed.

Because the magnetic separation step resulted in the elimination of all nucleic acids that did not contain at least some type 1 DNA, the result of the second separation step would be to end up with only nucleic acids that contain both type 1 and type 2 DNA. The second step could also be accomplished using other separation detection methods, such as bead size characterization, or filtration and bead counting, taught in Example 2. Also, if the second step was electrophoresis separation, a third step could be added for separation and quantification such as depositing the electrophoretically-separated bead complexes onto a miniarray on a glass slide and detection of fluorescence labels (e.g., Cy-3) on the beads by automated fluorescence scanning. This is a sensitive and efficient method that, theoretically, can detect as little as one bead per array spot.

Another format claimed in the present invention which facilitates automated processing and detection of nucleic acid aberrations is 96 well (or other format) plates.

If non-unique "painting probes" are used, nonspecific binding by the non-unique hybridization probes to the nucleic acid sample may be minimized through the use of non-specific sequence blocking techniques such as those disclosed by U.S. Pat. No. 5,447,841, and Pinkel et al., 85 Proc. Natl. Acad. Sci. USA 9138–9142 (1988), which are hereby incorporated herein by reference.

The first and second hybridization probes may include RNA or DNA sequences such that the complementary nucleotide sequences formed between the hybridization probes and the target sequence may be two DNA sequences or an RNA and a DNA sequence.

The detection and quantification of isolated sequences containing type 1+2 sequences can be done using a variety of available methods, such as total DNA measured by spectrophotometry, various labels on the beads or probes such that they can be measured by chromatography, fluorescence, isotopes, and the like. Any analytically detectable label that can be attached to or incorporated into a hybridization probe or bead may be used in the present invention. An analytically detectable label refers to any molecule, moiety, or atom that can be analytically detected and quantified. Methods for detecting analytically detectable labels include, but are not limited to, radioactivity, fluorescence, absorbance, mass spectroscopy, EPR, NMR, XRF, luminescence, and phosphorescence. For example, any radiolabel that provides an adequate signal and a sufficient half-life may be used as a detectable label.

Fluorescent molecules, such as fluorescein and its derivatives, rhodamine and its derivatives, cyanide and its derivatives, dansyl, umbelliferone and acridimium, and chemiluminescent molecules such as luciferin and 2,3-dihydrophthalazinediones may also be used as detectable labels. As discussed herein, the nucleotide sequences used in hybridization probes may themselves function as detectable labels where the bases forming the nucleotide sequence are quantified using techniques known in the art.

Also, beads can be detected by directly counting as in Example 2 using different bead sizes, or by fluorescence intensity emitted from minispots, on a glass slide detected by automated fluorescence scanning. A large number of fluorescent tags and methods for attaching to nucleic acid probes and beads are now available commercially.

A nucleotide sequence aberration frequency (e.g., number of aberrant sequences per total number of cells from which the DNA sample was obtained) may be determined based on the signal generated from the detectable marker using a calibration curve. The calibration curve may be formed by analyzing a sample of cells having a known nucleotide sequence aberration frequency. For example, the FISH method for detecting chromosome translocations may be used to determine the nucleotide sequence aberration frequency rate of a sample of cells. Then, by serially diluting the sample of cells and assaying the cells according to the method of the present invention, a calibration curve may be generated. Alternative methods for generating a calibration curve are within the level of skill in the art and may be used in conjunction with the method of the present invention.

Interchromosomal rearrangements typically are of two types: translocations and dicentrics. Translocation are rearrangements that result in two derivative chromosomes that have one centromere each, whereas dicentrics are rearrangements that result in one derivative chromosome with two centromeres and another with no centromeres. When quantifying the frequency of interchromosomal rearrangements, it is often useful to know whether they are translocations or dicentrics. Translocations persist for a lifetime, while dicentrics, diminish with time. Dicentric chromosomes may be identified according to the method of the present invention by using first and second hybridization probes that each hybridize to the centromere of a different chromosome. DNA probes specific to the centromeres for almost all human chromosomes are now commercially available for (e.g., Ventana Medical Systems, Inc., Tucson, Ariz.; Oncor, Inc., Gaithersburg, Md.).

The present invention also relates to a kit for separating and quantifying nucleic acid aberrations and diagnosing diseases according to the methods of the present invention. In general, the kits of the present invention include a first hybridization probe and a second hybridization probe as described herein. The kits may also include a complexing agent bound to a magnetic responsive bead, one or more complexing agents bound to a bead that is magnetically nonresponsive. The kit may also be designed for a 96-well plate format, either with or without magnetic beads, as described herein as well as instructions for using the kit. The kits may also include beads of different sizes, colors, and detectable markers.

All publications, patents, patent applications, and commercial materials cited herein are hereby incorporated by reference.

7. EXAMPLES

The following examples are given to illustrate various embodiments which have been made within the scope of the present invention. It is to be understood that the following examples are neither comprehensive nor exhaustive of the many types of embodiments which can be prepared in accordance with the present invention.

Example 1

This is an example of a method that can be used to separate and quantify DNA with two unique and non-overlapping sequences. In this example, the sequences (identified here as Type 1 and Type 2 DNA) span 0.8 kb each and are about 17 kb apart on a contiguous 18.2 kb double stranded DNA molecule. Importantly, these sequences are too far apart for detection by PCR, which is limited to less than about 10 kb, and the 18.2 kb extended DNA molecule is too small for detection by FISH which is generally limited to the detection of condensed DNA such as that in metaphase chromosomes. Hence, the separation and detection demonstrated in the present example could not have been accomplished using available methods. It is also important to note that the DNA molecule selected for this example could just as well have been the result of a rearrangement between Type 1 and Type 2 DNAs, where, for example, Type 1 DNA is from one chromosome and Type 2 DNA is from another chromosome. Hence, the method of the present example can be used to separate and quantify any rearrangement for which complementary Type 1 and Type 2 DNA probes are available or obtainable. A large number of probes are now available for sequences that flank DNA fusion points associated with cancer-related chromosomal rearrangements, such as the t(9;22) observed in human myelogenous leukemia and described in Tkachuk et al., 250 Science 559–562 (1990), and U.S. Pat. No. 5,487,970.

It is also possible to use the method of the present example to separate and quantify random rearrangements that may be induced by clastogenic agents such as radiation and certain chemicals. In this case, the object would be to sample as large a fraction of the genome as possible by selecting the largest chromosomes as hybridization targets. For example, if Type 1 DNA probes were selected to be unique to chromosome 1 (e.g., a sequence, or cocktail of sequences, complementary to one or more genes located on chromosome 1, or a human chromosome 1 centromeric probe available from Oncor, Inc., Gaithersburg, Md.), and Type 2 DNA probes were selected to be unique to chromosomes other than chromosome 1 (e.g., a cocktail of composite probes complementary to gene sequences on chromosomes 2 through 4), any chromosome 1 with Type 2 DNA probes attached would be the result of a translocation between chromosome 1 and chromosomes 2, 3, and/or 4.

The present method would quickly separate and quantify such events. A large number of chromosome-mapped gene sequences are now available from human genome projects. In fact, a chromosome-specific physical map now exists for over 30,000 human genes (Deloukas et al., Science 282, 744–746; 1998) and a large number of these genes have sequences published on the Internet (e.g., www.ncbi.nlm.nih.gov). Importantly, anyone skilled in the art can use available methods (described below) and these published sequences to synthesize biotinylated probes that are complementary to the available gene sequences and thus make biotinylated probes (or cocktails of composite biotinylated probes) that are unique to any human chromosome, even unique to many regions of human chromosomes. The probes could also be painting probes (e.g., commercially available from Vysis, Inc., or Ventana Medical Systems, Inc. (Tucson, Ariz.). For painting probes, non-specific hybridization can be reduced using available non-specific hybridization blocking methods (Pinkel et al., Proc. Natl. Acad. Sci. USA 9138–9142, 1988; U.S. Pat. No. 5,447,841). By using chromosome-specific (unique) probes (e.g., complementary to gene coding sequences) for hybridization to Type 1 DNA, the first separation step would be assured to be very clean. For the special case of separation and quantification of dicentric chromosomes (i.e., interchromosomal rearrangements resulting in a chromosome with two centromeres), centromeric probes can be used for both Type 1 and Type 2 DNA. These probes are available commercially for essentially all human chromosomes (e.g., Oncor, Inc).

Target DNA

Figure 3A:
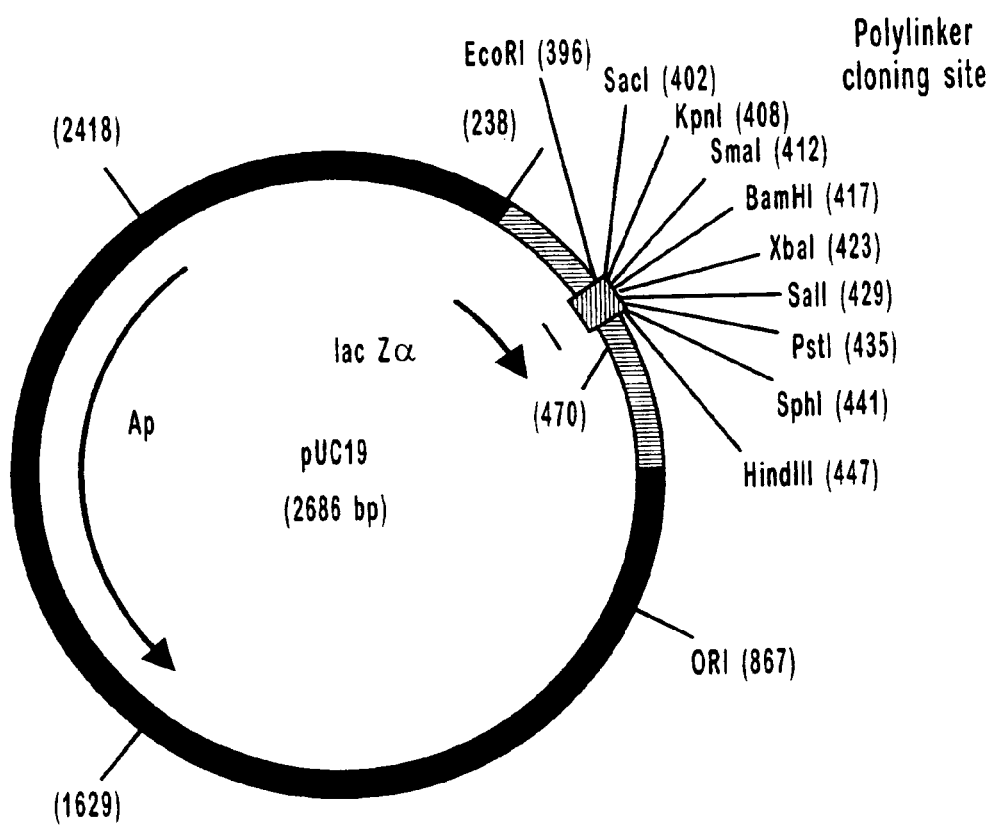
Figure 3B:
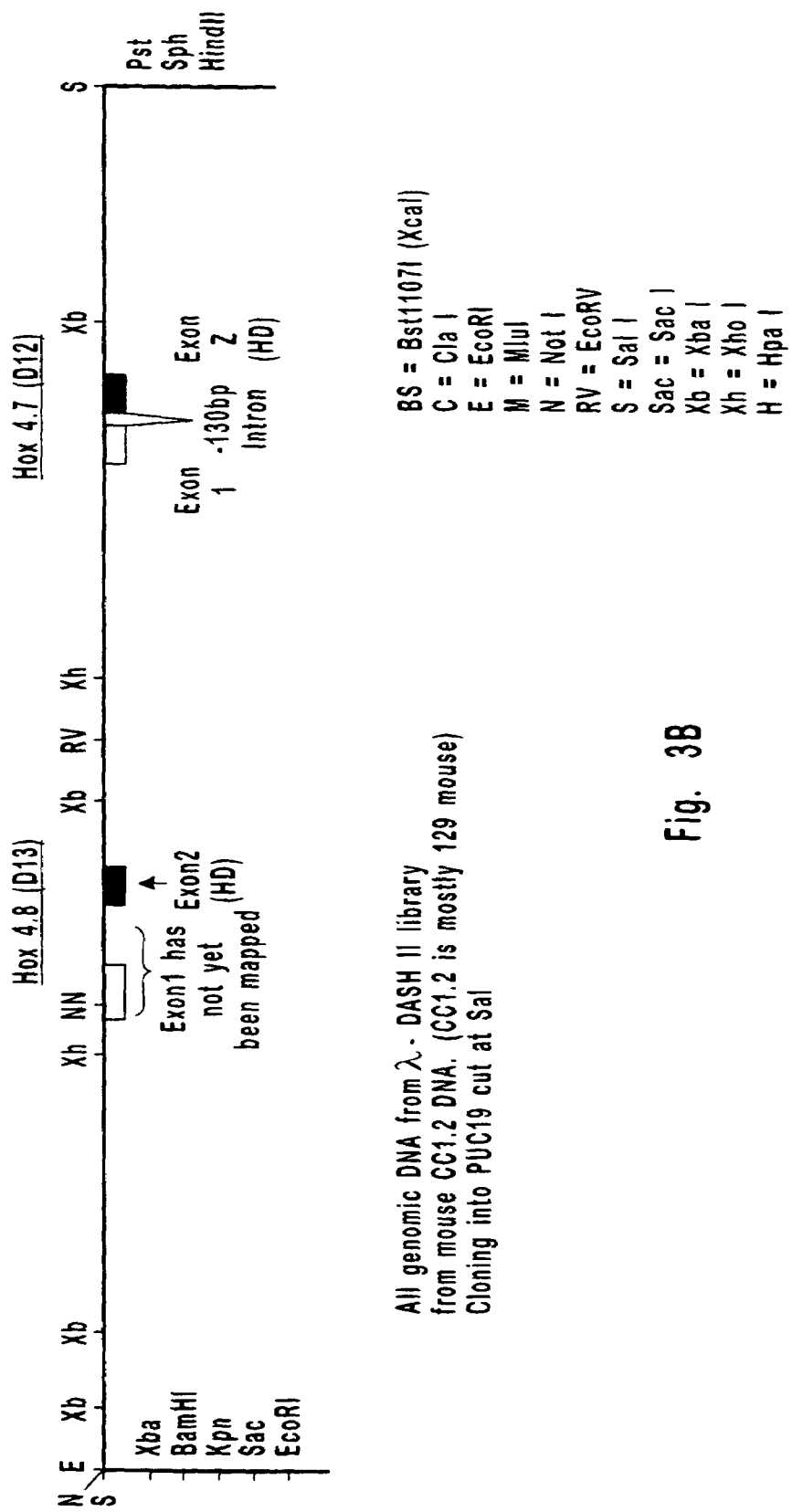

The DNA used as hybridization target for this example of the present method is an 18.2 kb insert in a pUC19 plasmid (FIGS. 3A–B). The double-stranded DNA insert was positioned at the plasmid's SalI site so that it could be removed from the plasmid by digestion with SalI restriction enzyme.

The DNA insert was amplified by growing the plasmid in E. coli bacteria as follows. First, 4.2 μg of plasmid DNA was diluted in 1000 μl distilled deionized water. One μl of this solution was then used to electroporate the DNA into E. coli using a Bio-Rad electroporation apparatus (Bio-Rad, Inc.). The E. coli were immediately collected and placed in an incubator at 37 C for 30 min, followed by plating on agar medium (Luria-Bertani with ampicillin), and incubating at 37 C overnight. The next day, individual colonies were collected and grown overnight in 5 mL of liquid medium (Luria-Bertani with ampicillin).

The plasmid DNAs were purified using a QIAprep-spin plasmid kit (#27104) according to manufacturer's protocol in QIAprep Miniprep Handbook, April 1998, pp. 18–19 (Qiagen, Inc., 28159 Stanford Ave., Valencia, Calif. 91355).

The purified plasmid DNAs were then digested with SalI to permit extraction of the 18.2 kb target DNA insert. The Sal I restriction enzyme was obtained from Sigma at a stock concentration of 10,000 units/mL. To the plasmid solution (30 μg/132 μl TE) was added 15 μl SalI stock solution, 30 μl Sal I buffer from Sigma, and 135 μl distilled deionized water. After mixing, the reaction mixture was incubated at 37 C for 1 hour, then maintained at 4° C. overnight. Before use, solutions were changed to fresh aliquots of B&W buffer (10 mM Tris-HCl, pH 7, 1 mM EDTA, 2 M NaCl).

Then, the 18.2 kb target DNAs were extracted using phenol/chloroform/isoamyl alcohol (25:24:1; v:v:v) as described in "Molecular Cloning: A Laboratory Manual", Second Edition, Sambrook et al., Eds. (1989) and washed with ether. DNAs were precipitated with 100% ethanol after adding 3 M NaOAc to final concentration 0.3 M. The precipitated solutions were then stored at 0° C. for 2 hours, centrifuged, and the supernates removed. Residues were washed with 70% ethanol and dried at room temperature in air.

The extracted 18.2 kb DNAs were verified by agarose gel electrophoresis using standard methods.

DNA Probes

For the present example, the DNA sequences (50mers) used as hybridization probes were synthesized using an Applied Biosystems Model 3948 synthesizer (Perkin-Elmer, Applied Biosystems Division, Foster City, Calif.) and standard methods known to those skilled in the art of DNA oligonucleotide synthesis to be uniquely homologous with the terminal ends of the 18.2 kb insert. First, about 1 kb of DNA was sequenced at each terminal end of the 18.2 kb insert. Then, four 50 bp complementary sequences, each with uniquely different sequences, were synthesized with homology to one end of the DNA insert (Type 1 Probes) and another four 50 bp complementary sequences synthesized with unique homology to the other end of the DNA insert (Type 2 Probes).

The probes were then biotinylated by covalently attaching biotin TEG phosphoramidite (Cat. #10-1955-02, Glen Research, Sterling, Va.) to the 5' end of the DNA probes via a 15 atomic bond spacer arm. The result is that no probe has more than one biotin attached to it, and hence there is no unbound biotin on the probe after complexing with avidin on the solid support and washing. This is useful in the present invention because all probe types (as well as any other attachments to the beads such as probes for detection and peptides for other unique complexing agents) can use biotin as complexing agents to attach them to the avidin-coated beads as long as the attachments to the beads of different probe types are performed in separate solutions. Using a spacer arm greater than 10 to 12 atomic bonds eliminates potential binding problems between the biotinylated probes and the beads, and also facilitates subsequent hybridization of the probe to the target DNA (A. J. Ninfa and D. P. Ballou, "Fundamental laboratory approaches for biochemistry and biotechnology", pp. 102–103, 1998, Fitzgerald Science Press, Inc., Bethesda, Md.).

The sequences of the terminal ends of the 18.2 kb DNA and the unique 50mer probes are shown in FIG. 4. Sequencing of the ends of the 18.2 kb DNA was performed using ABI Prism BigDye Terminators and cycle sequencing with Taq FS DNA Polymerase. DNA sequences were collected and analyzed on an ABI Prism 377 automated DNA sequencer (Perkin-Elmer, Applied Biosystems Division, Foster City, Calif.).

Beads

Two types of beads were used in this example, magnetically-responsive beads purchased from Dynal AS, Oslo, Norway, and magnetically non-responsive beads purchased from Bangs Labs, Fishers, Ind.

Figure 5:
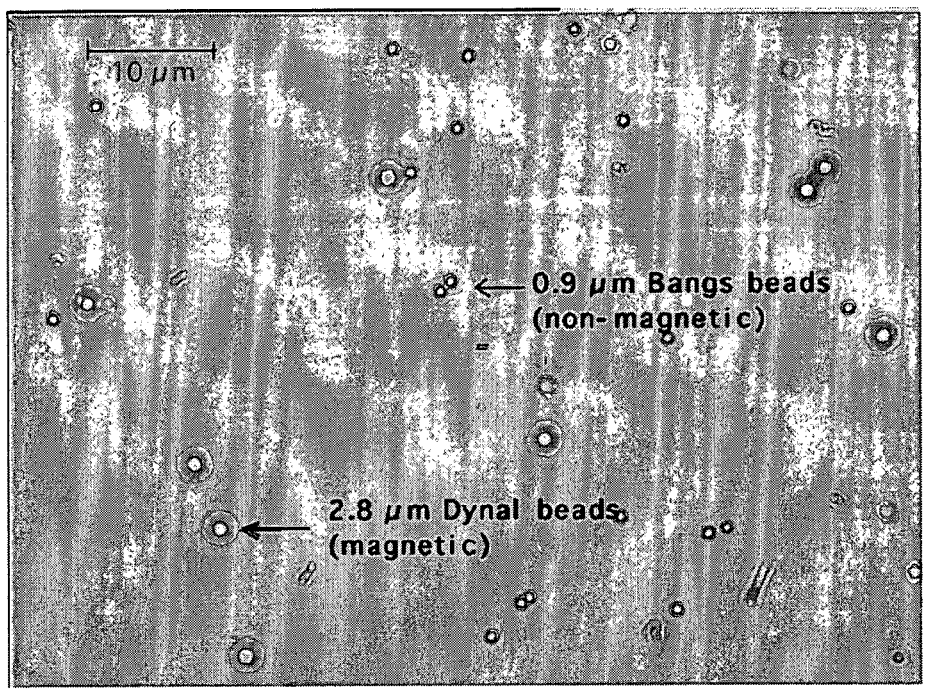
FIG. 5 shows Dynal and Bangs beads observed using a light microscope at 1000× magnification. In this case, beads were taken from the stock solutions, mixed, placed on a glass microscope slide, and viewed under oil immersion.

The magnetically responsive beads were "Dynabeads Streptavidin" (Product #112.05), which are 2.8 μm in diameter and coated with streptavidin. The magnetically non-responsive beads were from Bangs Labs (Catalog #CP0 IN), which are 0.94 μm in diameter and also coated with streptavidin. The two bead types are seen in FIG. 5 (1000× magnification, light microscope).

The two bead sizes selected provided a simple and very useful means to verify results as the technology was being developed. That is, hybridization and separation efficiencies are rapidly determined by observing bead types at various stages using a light microscope.

Attach Probes to Beads

The biotinylated probes were then attached to the Dynal avidinylated beads as follows. First, 0.2 mL TE buffer solution (10 mM Tris-HCl, pH 7.5, 1 mM EDTA) containing 2.8 μg Probe 1, 2.8 μg Probe 2, 2.8 μg Probe 3, 2.8 μg Probe 4, and 1.3 μg of a biotinylated T7 22mer (Cat. #300322, Stratagene.com) was prepared. Probes 1 through 4 were the 50mers that were synthesized to be complementary to the DNA on one end of the 18.2 kb target DNA (Type 1 DNA). The T7 22mer is a unique probe used here for detection purposes only, i.e., it provides an option for subsequent hybridizations with a fluorescent marker to detect the presence of the Dynal beads.

Next, the Dynal beads (2 mg/0.2 mL) were washed once with 1 mL of B&W buffer solution and resuspend in 0.2 mL B&W buffer. For the magnetically-responsive Dynal beads, washing was accomplished using the Magnetic Particle Concentrator (MPC) (Dynal AS).

Finally, the solution of Probes 1 through 4 and T7 was mixed with the solution of Dynal beads. This mixtures was then gently shake for 1 hour at room temperature. The beads were then washed four times with B&W buffer, 0.4 mL each. Next, the probe-coated Dynal beads were resuspended in 0.4 mL B&W and stored at 4 C.

The biotinylated probes were attached to the Bangs avidinylated beads as follows. Similar to the preparation of the Dynal beads described above, 0.2 mL TE buffer solution was prepared containing 2.8 μg Probe I, 2.8 μg Probe II, 2.8 μg Probe III, 2.8 μg Probe IV, and 12 μg of a biotinylated hemagglutinin (HA) peptide. Probes I through IV were the 50mers that were synthesized to be complementary to the DNA on the other end of the 18.2 kb target DNA (Type 2 DNA). The HA peptide was synthesized using an Advanced ChemTech Model 348 peptide synthesizer (Advanced ChemTech, Inc., www.peptide.com) and was biotinylated by attaching a single biotin molecule to the terminal amino-end of a 6 carbon spacer molecule that was then attached via its carboxyl end to the terminal amino end of the HA peptide. The biotinylated HA peptide was then attached to the Bangs beads to be used subsequently as a complexing agent for stage 2 separation involving anti-HA antibody.

Next, the Bangs beads (2 mg/0.2 mL) were washed once with 1 mL of B&W buffer followed by one wash with 1 mL of TE. The beads were resuspended in 0.2 mL B&W solution. For the Bangs beads (which were non-magnetic), washing was accomplished using centrifugation.

Finally, the solutions of biotinylated probes I through IV and biotinylated HA peptide were mixed with the solution of Bangs beads. This mixture was gently shaken for 1 hour at room temperature, and then the reaction solution was removed by centrifugation. The beads were then washed once with 1:1 (v/v) B&W buffer and TE, 0.4 mL each. The probe-coated Bangs beads were then resuspended in 0.4 mL B&W and stored at 4° C.

Hybridization and Magnetic Separation (Usually Stage 1 Separation)

The 18.2 kb target DNA was hybridized to probes on beads. Selected amounts (typically μg quantities) of the 18.2 kb DNA were dissolved in 300 μl 70% formamide denaturing solution (210 μl formamide, 30 μl 20×SSC, 60 μl distilled deionized water), then heated to 70 C for 5 min. The hot solution was immediately added to the cooled solution containing 10 μL Dynal beads (2 mg/0.2 mL TE), 10 μl Bangs beads (2 mg/0.2 mL TE), 75 μl 20× SSC, and 16.6 μl distilled deionized water. After mixing, 4.2 μl 10% SDS and 4.2 μl salmon sperm DNA were added. Hybridization was carried out in an incubator for 15 hours at 40 C with constant rotation of about 1 rpm. After cooling to room temperature, MPC was used to remove hybridization solution and unhybridized Bangs beads. The remaining beads were then washed once with 600 μl 1×SSC, 0.2% SDS, for 6 min at room temperature. The MPC washing step was then repeated. The beads were next washed with 600 μl solution of 0.1×SSC, 0.2% SDS, for 10 min at room temperature. The MPC step was repeated, and then the beads were washed three times with distilled deionized water. The beads were next resuspended in 500 μl PBS. A 50 μl aliquot was taken as solution B ($1.34 \times 10^4$ Dynal beads/μL), from which 5 μl was mixed with 45 μl PBS to become solution C ($1.34 \times 10^3$ Dynal beads/μL). The remaining 450 μl solution was removed by MPC and 45 μl PBS was added to become solution A ($1.34 \times 10^5$ Dynal beads/1 μL). Note: PBS buffer is 0.14 μg $NaH_2PO_4$, 0.79 μg $Na_2HPO_4$, 8.1 μg NaCl in total 1000 mL distilled deionized water.

Filtration Separation

If the magnetically responsive beads in solutions A, B, and C above were selected to be larger than the magnetically non-responsive beads, then Stage 2 separation could be accomplished by cutting the DNA connecting the two bead types (i.e., the 18.2 kb DNA molecule hybridized to both bead types can be digested by DNase or released from the magnetically-responsive bead via a cleavable linker) and filter the solution through a filter selected to permit only the smaller non-magnetic beads to pass through. The number of small beads could then be quantified using available methods such as a Coulter counter. Also, if a cleavable linker is used to release the DNA molecule from the magnetic bead then the DNA would be pulled along with the small non-magnetic bead through the filter and would thus permit recovery of the target DNA. Importantly, the number of small beads recovered after filtration should be proportional to the number of target DNA molecules (i.e., Type 1+Type 2 DNA) in the hybridization solution. An example of the filtration method is described in Example 2 below.

Antibody-Peptide Separation

Attach antibody to glass slides. Streptavidin coated microscope slides obtained from Cell Associates, Inc. (www.cel-1.com) were washed 3 times with B&W buffer solution, then immersed in 20 mL solution containing 100 μg anti-HA-biotin (i.e., 10 mL TE, 9.5 mL Tris, 0.5 mL of 200 μg anti-HA-biotin/mL). The slides were shaken for 30 min at room temperature, then allowed stand at room temperature for 18 hours. Next, the slides were washed five times (2 min each) with PBS. After air drying at room temperature, the slides were stored at 4 C. The anti-HA-biotin was purchased from Boehringer Mannheim Corporation (Indianapolis, Ind.). Then, 1 μl each of solutions A, B, and C (from Stage 1 separation described above) was placed on the anti-HA coated slide at room temperature. After about 30 min, but before the 1 μl spots were dry, the slide was transferred into a slide box with a small amount of water in the bottom of the box (the water should not come in direct contact with the slide). The slides were incubated at 4° C. overnight, then washed twice with PBS and once with distilled deionized water. The slides were then dried at room temperature.

Detection and Quantification

Figure 6:
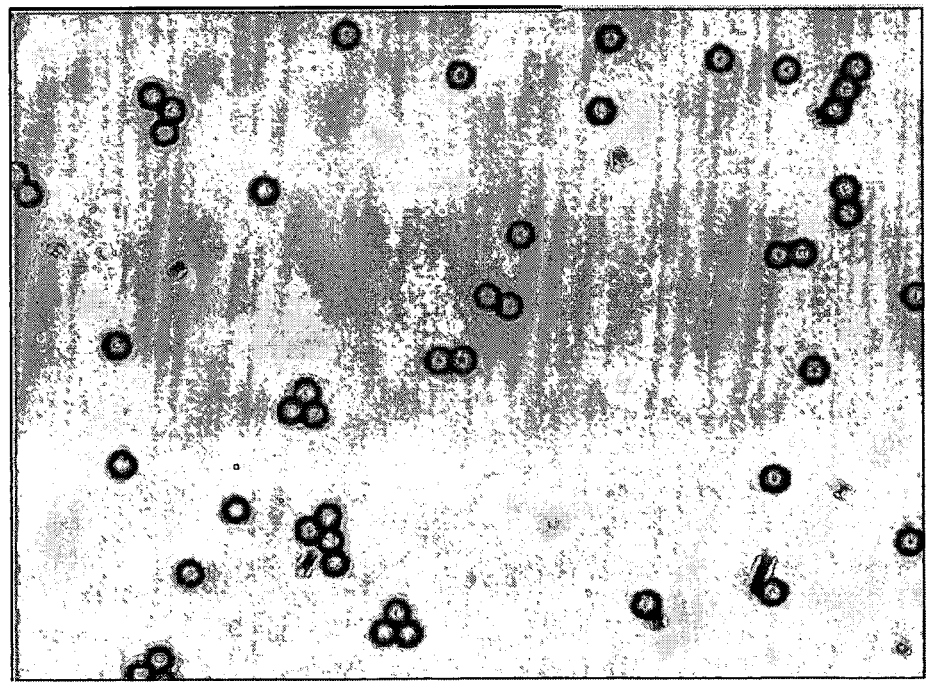
FIG. 6 shows a microscope image of beads deposited on a glass slide after the bead solution (Dynal+Bangs) had been subjected to magnetic separation, but without hybridization to the 18.2 kb DNA. Note that only Dynal beads are seen (the few small dots are dust on lens as they can also be seen on the other images).

Light microscopy. The beads deposited on the slides were then viewed using a Nikon microscope at 1000× total magnification (100× objective and 10× eyepiece). FIG. 6 shows a microscope image of a bead solution B (described above) deposited on a slide after probe attachment and magnetic separation, but without hybridization to the 18.2 kb target DNA. Note that no Bangs beads are observed. This demonstrated that Bangs beads are washed away during the magnetic separation step if not connected to the Dynal beads via hybridization to the 18.2 kb DNA molecule.

In contrast, FIG. 7 shows a microscope image of bead solution B which was hybridized to the 18.2 kb DNA. In this case, the bead-probe complexes were hybridized to the 18.2 kb DNA followed by magnetic separation as described above under "Hybridization and Magnetic Separation." Note that many of the smaller Bangs beads were present in FIG. 7 and were pulled along during the magnetic separation step by their attachment via hybridization to the same DNA molecule that the Dynal beads were hybridized.

Fluorescence scanning. In addition to light microscopy analysis, beads deposited on glass slides have also been analyzed using a fluorescence scanner. Fluorescence intensities were measured of 0.1 $\mu$l spots of beads deposited in an array format on a glass slide. The measurements were made using a Molecular Dynamics fluorescence scanner (Avalanche model). Each spot contains an average of about 33 Dynal beads and was about 1 mm in diameter. After depositing on the slide, the beads were hybridized with a Cy-3 labeled 22mer complementary to the T7 22mer that was previously attached to the Dynal beads. The complementary 22mer was synthesized using standard methods and a Cy-3 molecule was attached to the 5' end of the 22mers using Cy3-CE-Phosphoramidite (Glen Research, Sterling, Va.). Based on the present results, the fact that each streptavidin-coated Dynal bead can attach about 500,000 oligonucleotides (Dynal AS, Oslo, Norway), and the detection limit of commercially available fluorescence scanners which are on the order of 1 to 10 Cy-3 per $m^2$ (Bowtell, 21 Supplement, Nature Genetics page 31, 1999), the method described herein should be able to detect as little as a single bead deposited on a glass slide using Cy-3 labeling and a commercially-available fluorescence scanner. Similar detection limits would be expected for other common fluorescence labels. In practice, each bead type could be tagged in advance and thus identified at any stage of separation using a fluorescence scanner.

Particle counting. As described below in Example 2, if beads of different sizes are used with the present technology, each size coated with a unique probe, then the different sized beads can be selected by filtration and counted using a particle counter (e.g., from Coulter). This is a very quick, accurate, and low-cost method to quantify the number of beads which, after hybridization and magnetic separation, would be proportional to the number of target DNA molecules (or other target objects) in the analysis solution (see Example 2 for details).

It is also possible (as described in Example 2) to eliminate the filtration step by using a particle counter that measures both number of particles and their sizes (e.g., the Multisizer II by Coulter). In this case, distributions of particle sizes would be obtained and the number of beads of any selected size can be quantified by integrating the distributions (e.g., see Examples 6 and 7).

Electrophoresis Separation

It is also possible to perform separation using electrophoresis of the magnetically non-responsive beads, if such beads are selected to be electrically charged (e.g., this would permit the use of electrophoresis for Stage 2 separation and antibody-peptide separation for Stage 3). An experiment was performed in which two bead types were used, magnetically-responsive beads coated with amino groups (positive surface charge) and magnetically non-responsive beads coated with carboxylic acid (negative surface charge). The beads were from Bangs Labs (#MC05N, magnetic; #DC04, non-magnetic). The beads were selected to have two different colors, the magnetic beads were brown and the non-magnetic beads were green. Both bead types were about 1 $\mu$m diameter.

A 2 mm hole was drilled through a 10 mL plastic pipette (the hole was drilled at the 5 mL mark through one side only) and the pipette submerged in a standard TAE electrolyte buffer (pH 8.3) of a standard electrophoresis apparatus. The two types of beads were then mixed 1:1 in TAE buffer (pH 8.3) and 1 mL injected through the hole in the center of the pipette. The electrophoresis was carried out at 5 Volts per cm and a photograph taken at the start of the electrophoresis and again at +20 min. The results clearly showed that the green and brown beads were mixed at T=0 but were separated by about 1.5 cm at T=20 min (i.e., the negatively charged non-magnetic beads moved about 0.75 mm per min). This demonstrated the feasibility of using electrophoresis to separate non-magnetic beads from magnetic beads.

Based on these electrophoresis results, the magnetic separation results provided in this example, and the electrophoretic mobility measurements of similar beads made by Ottewill et al., Kolloid Zh., 218, 34 (1967), it is apparent that a magnetic bead with essentially neutral surface charge should be pulled along with the electrophoretically-responsive non-magnetic beads if the beads were connected to the same DNA molecule in a buffered solution. Magnetically-responsive beads with various surface charges (including essentially neutral surface charge) are commercially available (e.g., Bangs Labs, Fishers, Ind.).

Example 2

As discussed above, Stage 2 separation and quantification can also be accomplished by particle counting and size distribution analysis.

Filtration. For example, if Stage 1 separation is by magnetic force and Stage 2 is by filtration of beads, then the magnetically responsive beads would simply be selected to be larger than the non-magnetic beads. This would permit rapid separation of magnetically-responsive beads from non-magnetic beads. Because the only magnetically non-responsive beads remaining after Stage 1 separation are those complexed with magnetically-responsive beads via hybridization to the same contiguous nucleic acid molecule, the number of non-magnetic beads after Stage 1 would be proportional to the number of target nucleic acid molecules in the hybridization mix.

To facilitate separation of the beads by filtration, Stage 1 could be followed by detaching DNA from beads (e.g., via DNase treatment or cleavable linker) and filtering the beads through a filter that only permits the smaller non-magnetic beads to pass through. The smaller beads could then be counted using available particle counting technologies (e.g., Coulter counter) or quantified using available technologies such as fluorescence, flow cytometry, spectrophotometry, etc. Commercially available beads have a large number of colors and fluorescence wavelengths (e.g., Bangs Labs.).

FIGS. 5, 6, and 7, and Table I provide results that demonstrate the successful separation and quantification of target DNA molecules using a combination of magnetically-responsive and magnetically non-responsive beads, each type differing in size. FIG. 5 is a photomicrograph of the two bead types used in this example. The magnetically-responsive beads are 2.8 μm diameter and the non-magnetic beads are 0.94 μm diameter (beads are described in Example 1). FIG. 6 shows that all of the magnetically non-responsive beads are eliminated (washed away) during magnetic separation if hybridization of the DNA molecule is not performed to both the magnetic and the non-magnetic beads. In contrast, if hybridization is performed then some of the small beads are pulled along with the large beads during magnetic separation, as seen on the glass slide in FIG. 7.

If instead of depositing on a glass slide after magnetic separation (as was done in FIG. 7), the beads are separated from each other by detaching the hybridized DNA by, e.g., DNase treatment or a detachable linker between the magnetic bead and the hybridized DNA, and pass the beads through a 2 μm filter, the 2.8 μm magnetic beads would be too large to pass through the filter resulting in a filtered solution of only the non-magnetic beads (see data in Table I). These are the magnetically non-responsive beads that were previously hybridized to the same contiguous piece of DNA as the magnetic beads and thus were pulled along during magnetic separation. Note that after magnetic and filtration separation the number of these small beads recovered would be proportional to the number of Type 1+Type 2 DNA in the hybridization mix (this would be true for the present example as well as for target DNAs obtained from a human blood sample). The methods used to obtain the results in FIGS. 5, 6, and 7, are identical to those described in Example 1. The methods used to obtain the data in Table I are also identical to the methods in Example 1 for DNA target, DNA probes, beads, attachment of probes to beads, hybridization, and magnetic separation.

In Example 2, i.e., where Stage 2 separation is by filtration or size distribution analysis, the magnetic separation step in Example 1 is followed by detaching the DNA from the beads using DNase treatment (DNase I from Gibco BRL, Frederick, Md.) resulting in the beads becoming free in solution. One μl of the DNase I stock solution was diluted in 405 μl glycerol and 405 μl NTB buffer. The NTB buffer comprises 0.5 M Tris-HCl pH 7.5, 0.1 M MgSO$_4$, 1 mM dithiothreitol, and 500 g/mL bovine serum albumin (Fraction V, Sigma). Then, 22 μl of the diluted DNase solution was added to 44 μl of the bead solution to be DNA digested (i.e., the beads were in 44 μl 3xNTB). The solution of beads was then passed through a filter that permits only the small beads to pass through, in this example, a filter with 2 μm diameter circular pores (polycarbonate membrane filter available commercially from Millipore, Fisher Scientific Catalog #MP 013 00). Associated syringe filter holders are also commercially available to perform the filter operation (used for the present example, Millipore Stainless Steel 13 Filter Holder, Fisher Scientific Catalog Number XX-30 012 00).

The number of beads in the filtered solution can then be quantified using available methods, e.g., a Coulter counter, microscopy, fluorescence scanning, flow cytometry, spectrophotometry, etc. A preferred method of bead quantification is by counting in a Coulter counter. At this stage, only the small beads that were hybridized to a Type 1+Type 2 DNA are present in the solution, hence the number of these beads are proportional to the number of Type 1+Type 2 DNA sequences in the initial sample (e.g., a blood sample). The proportionality constant can be obtained from laboratory measurements using standard mixes of target DNA and bead-probe complexes. That is, just as routinely done for most kinds of measurement technologies, a standard curve would be used to convert the measured number of beads to the number of target DNAs in the original sample.

Table I presents results obtained from a filtration experiment. In this case, three different solutions were filtered using the 2.0 μm Millipore filter system described above: (1) saline only without beads, (2) a solution containing both Dynal and Bangs beads which has been subjected to the complete hybridization conditions and reagents except that the 18.2 kb DNA was not included in the hybridization mix, and (3) a solution containing both Dynal and Bangs beads and hybridized with 20 μg of the 18.2 kb target DNA. The results demonstrate that without hybridization to the 18.2 kb DNA target molecule, the Bangs beads are not pulled along with the Dynal beads during magnetic separation. That is, without hybridization there is no significant difference between the bead counts and the saline background. This is due to the removal of all Bangs beads during the magnetic separation step and subsequent removal of all Dynal beads during the filtration step.

TABLE I

Coulter Counter Results for Three Types of Filtered Solutions

| | Mean Counts/100 μL | SD |
|---|---|---|
| Filtered Saline | 145 | 109 |
| Filtered beads*, w/o hybrid | 159 | 20 |
| Filtered beads**, with hybrid | 2910 | 300 |

Table I shows particle counter results for three types of filtered solutions, filtered using 2.0 μm Millipore filters (Fisher Scientific Cat. No. TTTP 013 00), wherein a Coulter counter Model Zf was used with a 30 μm aperture tube to measure the indicated solutions. The means and SDs are based on multiple measurements.

In contrast, when hybridization is done then the Bangs beads are detected after filtration. This is due to the fact that both Dynal and Bangs beads are hybridized to the same 18.2 kb DNA molecule. Hence, the Bangs beads are pulled along by the Dynal beads during the magnetic separation step, released from the Dynal beads by DNase treatment, and finally separated from the Dynal beads by filtration through a 2.0 μm filter that only permits the Bangs beads to pass through. The results for the conditions of the present experiment show a count signal that is 20 times above background, providing a very accurate measurement.

The data in Table I suggest a detection limit for this method of about 5 ng target DNA or about 1000 cell equivalents of DNA. This is highly competitive with available detection methods (Duggan et al., 21 Nature Genetics (Supplement) 10–14 (1999)).

More generally, this approach can be used to detect rearrangements in any nucleic acid molecule larger than about 10 bp for which suitable hybridization probes are available or obtainable, including DNA at any level of organization from single stranded to metaphase chromosomes. For example, DNA probes for abl and bcr (which are available) could be used together with the technology described here to rapidly separate and quantify marker chromosomes for human chronic myelogenous leukemia, i.e., so-called Philadelphia chromosomes involving a very specific translocation between chromosomes 9 and 22. The abl and bcr genes flank the fusion point on chromosome 22 (Tkachuk et al., 250 Science 559–562 (1990)). To quantify these types of rearranged chromosomes using the present invention, a uni-biotinylated probe (only one biotin per probe) homologous to bcr is complexed to the avidin-coated Dynal paramagnetic beads and a uni-biotinylated probe homologous to abl to the avidin-coated Bangs non-magnetic beads and then perform the separation and quantification procedures as described above.

It is also an embodiment of the present invention to employ methods for the specific detachment of the DNA from the magnetically-responsive bead prior to filtration. If the detachment site was between the DNA and the bead then the complete DNA molecule would remain attached to the small non-magnetic bead and would therefore pass through the filter and be isolated together with the small beads. This would permit further evaluations/diagnostics of the isolated target DNA. Site-specific detachment can be accomplished using available cleavable linkers.

Both specific and random rearrangements can be quantified using this approach. The 9;22 translocation described above is an example of a specific rearrangement. An example of the quantification of random rearrangements is if we selected a probe with unique homology to chromosome 1 (i.e., Probe 1) and a cocktail of composite probes with homology to other chromosome(s) but not to chromosome 1 (i.e., Probe 2). The more sequences of non-chromosome-1 targets covered by Probe 2, the more translocations would be detectable. Probe 1 would then be complexed with the 2.8 $\mu$m paramagnetic beads and Probe 2 would be complexed with the 0.94 $\mu$m non-magnetic beads. If, in this example, Probe 2 hybridizes to chromosome 1 then interchromosomal rearrangement has in fact occurred. These translocated chromosomes can then be separated and quantified using the method described above. It is expected that standard calibration curves would be obtained for each particular kind of detection kit, i.e., one for each specific rearrangement and one for a particular class of random rearrangements.

Size distribution analysis. If, after magnetic separation and DNA detachment (described above), the resultant solution of beads is analyzed using a particle sizer/counter (e.g., a Multisizer II by Coulter), the two bead types can be separated by their size distributions and the number of beads in each distribution quantified. This is illustrated in FIG. 8. It is seen that the distributions for the 4.4 $\mu$m beads and the 2.8 $\mu$m beads are well separated and that the number of beads in each distribution can be quantified by integration of the peaks. In contrast to Table I, the distributions in FIG. 8 show the results of a DNA separation experiment in which the magnetically non-responsive beads were larger than the superparamagnetic beads. In this case, the larger non-magnetic beads were selected to place the peak in a region of lower background counts. The materials and methods used to obtain the results in FIG. 8 were the same as those used for Table 1 with the following differences: FIG. 8 used 4.4 $\mu$m diameter magnetically non-responsive polystyrene beads coated with streptavidin (Bangs Labs, Fisher, Ind.) whereas Table 1 used 0.94 $\mu$m diameter magnetically non-responsive polystyrene beads coated with streptavidin (Bangs Labs); FIG. 8 used 5 $\mu$g of 18.2 kb target DNA whereas Table I used 20 $\mu$g of 18.2 kb target DNA; partial magnetic separation was done for FIG. 8 following DNase treatment to reduce (but not fully eliminate) the number of superparamagnetic beads to provide a lower background level while at the same time provide a 2.8 $\mu$m peak for comparison/illustration purposes; and for FIG. 8 the final bead concentration was diluted two-fold just before generating the bead size distributions using the Coulter Multisizer II. Note that when accounting for the differences in the amount of target DNA hybridized and final two-fold dilution, the results of Table 1 and FIG. 8 agree very well, i.e., 2910±300 non-magnetic beads were recovered in the experiment reported in Table I, while 322 non-magnetic beads were recovered in the experiment shown in FIG. 8. If the two experiments are normalized by the target DNA (5 $\mu$g v. 20 $\mu$g) hybridized and the two-fold dilution, the result in FIG. 8 of 322 non-magnetic beads would become 322×4×2=2576 non-magnetic beads, not significantly different from 2910 in Table I.

It should also be noted that the intention of the present invention is not to be limited by two sizes of beads, but rather that many beads sizes may be used in combination in a more complex and multiplexed system of separation and detection.

Example 3

This is an example of a method that can be used to separate and quantify nuclic acids (or chromosomes) with two unique and non-overlapping sequences, both on a contiguous nucleic acid molecule or chromosome. In this example, the two different sequences are identified as Type 1 and Type 2 nucleic acid sequences.

The method of the present disclosure includes, but is not limited to, the use of two kinds of microbeads. One kind of microbead is responsive to a magnetic field (e.g., Dynabeads Streptavidin, Product #112.05 from Dynal A/S, Oslo, Norway) and could be coated with biotinylated nucleic acid probes complementary to Type 1 nucleic acid sequences by attaching to the avidin on the surface of the magnetically-responsive beads. The other kind of microbead is not responsive to a magnetic field (e.g., streptavidin-coated polystyrene beads from Bangs Labs, Fishers, Ind.) and could be coated with biotinylated nucleic acid probes complementary to Type 2 nucleic acid sequences by attaching to the avidin on the surface of the magnetically non-responsive beads. The attachment of the two probe types to their respective kinds of beads would be performed in separate solutions. The magnetically non-responsive beads would also be coated with an electrochemiluminescence (ECL) marker, e.g., ruthenium (II) tris-bipyridine NHS ester. See Blackburn, et al. Clin. Chem. 37 (9), 1534–1539 (1991) for a description of detection using ECL labels.

In the present invention, the ECL marker would be attached to the magnetically non-responsive beads by, e.g., biotinylating the marker and attaching it to the beads either separately or in competition with the biotinylated probes. An example of DNAs and coated beads is illustrated in FIG. 9.

After coating the respective kinds of beads and washing away unbound reagents, the coated beads are mixed together in a hybridization solution containing the target nucleic acid (e.g., isolated DNA or metaphase chromosomes). Using hybridization reagents and conditions available in the art (e.g., see Example 1 for isolated DNA; the Example in U.S. Pat. No. 5,731,153 for metaphase chromosomes; and the hybridization methods in U.S. Pat. No. 5,447,841 for "painting" probes) the result is the hybridization of the probes on the microbeads to their respective homologous sequences on the target nucleic acid, which produces the hybridized complexes shown in FIG. 9.

The next step is magnetic separation. This is accomplished by first gently shaking the vial to obtain a homogeneous suspension of beads and then placing the vial in the Dynal magnet stand (Dynal A/S, Oslo, Norway) for 2 minutes to allow beads to migrate to the side of the tube. This is followed by removing the supernatant by aspiration with a pipette while the tube remains in the magnetic stand. The tube is then removed from the magnetic stand and fresh buffer is added. This separation step can be repeated and results in the removal of all DNA and beads that are not connected to magnetically-responsive beads via a contiguous target molecule, i.e., only the kinds of complexes shown in FIG. 9 should remain in the sample tube after magnetic separation.

Importantly, following magnetic separation, the only complex with the ECL label is in fact the one containing both Type 1 and Type 2 DNA. This could, for example, be a fusion between two different chromosomes such as those resulting from interchromosomal translocations, or it could be any two uniquely different sequences on a contiguous target nucleic acid molecule.

The next step is detection by ECL. This would be accomplished by adding vast molar excess of tripropylamine (TPA) to the buffer containing the magnetically separated bead complexes and then placing aliquots of the solution onto an electrode surface. A low voltage is applied to the electrode which triggers a cyclical oxidation and reduction reaction of the ruthenium metal ion which generates the emission of 620 nm photons. Methods and devices that can be used to detect and quantify the ECL label on the non-magnetic beads are described in Blackburn, et al. Clin. Chem. 37 (9), 1534–1539 (1991), and also in www.igen.com (i.e., the home page of IGEN International, Inc., which provides a commercially available instrument to detect ECL signals). Importantly, by keeping our magnetic-non magnetic bead complexes intact following magnetic separation (i.e., no DNase treatment) will permit direct measurement using IGEN's automatic sample processing system which employs a magnet to immobilize each sample during ECL measurement. The magnetic bead in our complex will serve as the immobilizing particle while the attached non-magnetic bead will contain the ECL label and hence produce the ECL signal.

Detection is illustrated in FIG. 9, which includes the Type 1+Type 2 DNA bead complex deposited on the electrode surface. A photon is emitted and detected by a photomultiplier tube (PMT) or other suitable detection system. Such detection systems are now available commercially (e.g., IGEN International, Inc.). For a given number of ECL labels per bead (which can be selected) the number of photons is proportional to the number of non-magnetic beads, which for a given probe/target nucleic acid protocol, is proportional to the number of contiguous Type 1+Type 2 target sequences in the sample.

More generally, this approach can be used to detect rearrangements in any nucleic acid molecule of sufficient size to hybridize one or more microbeads to each type of nucleic acid, and for which suitable hybridization probes are available or obtainable, including DNA at any level of organization from single stranded to metaphase chromosomes. Presently, commercially available microbeads range in diameter from about 50 nm to several mm. Fifty nm is equivalent to the length of about 50 bp of the DNA molecule and would probably be near the minimum distance required to hybridize one bead. Of course, the maximum distance will simply depend on the size of the target sequence. Alternatively, one could hybridize the magnetically-responsive microbead to the Type 1 nucleic acid and hybridize a nucleic acid probe with the ECL label attached directly to the probe without a non-magnetic bead to the Type 2 nucleic acid target. This should permit unique hybridization to target nucleic acid sequences larger than about 10 bp.

Both specific and random rearrangements can be quantified using this approach. For example, DNA probes for abl and bcr (which are available) could be used together with the technology described here to rapidly separate and quantify marker chromosomes for human chronic myelogenous leukemia, i.e., so-called Philadelphia chromosomes involving a very specific translocation between chromosomes 9 and 22. The abl and bcr genes flank the fusion point on the Philadelphia chromosome. To quantify these types of rearranged chromosomes using the present invention, we would attach the probe homologous to bcr to the superparamagnetic beads and the probe homologous to abl and the ECL label to the non-magnetic beads and then perform the separation and quantification procedures as described above.

An example of the quantification of random rearrangements is if we selected a probe with unique homology to chromosome #1 (i.e., Probe 1) and one or more probes with homology to any other chromosome but not to chromosome #1 (i.e., Probe 2). Probe 1 would then be complexed with the paramagnetic beads and Probe 2 (which could be a composite of several probes, including painting probes) would be complexed with the non-magnetic beads containing the ECL label. If both Probe 1 and Probe 2 are hybridized to the same chromosome then interchromosomal rearrangement has in fact ocurred. These translocated chromosomes can then be separated and quantified using the method described above. Standard calibration curves would be obtained for each particular kind of detection kit, e.g., one for each specific kind of rearrangement and one for a particular class of random rearrangements. For example, ECL intensity vs. rearrangements per cell, could be measured in standard samples of known rearrangement frequencies using standardized kit formats with demonstrated reproducibility.

Example 4

Avidin-coated magnetically responsive microbeads are complexed with biotinylated antibodies specific for the M allelic GPA protein (FIG. 10). Magnetically non-responsive microbeads are complexed with biotinylated antibodies specific for the N allelic GPA protein. The two types of bead-antibody complexes are then incubated with blood erythrocytes (the attachment of beads and complexing agents can be done in any order as long as they are unique). The resulting products are of three types: (1) erythrocytes bearing the M protein complexed to beads coupled to the anti-M antibody; (2) erythrocytes bearing the N protein complexed to bead coupled to the anti-N antibody; and (3) erythrocytes bearing both the M and N proteins complexed to both the beads coupled to the anti-M antibody and the beads coupled to the anti-N antibody.

Magnetic separation results in washing away all erythrocytes without magnetic bead attachments. Next, the complexing agents are simply digested with protease and the beads analyzed using the particle size distribution using the Multisizer II (Coulter, Inc.). Using different size particles for M and N results in a readily quantifiable number of non-magnetic particles which would be proportional to the number of MN erythrocytes. Information on GPA mutations and the methods to complex antibodies with the M and N allelic proteins on the surface of human red blood cells is available in Langlois, et. al, 236 Science 445–448 (1987), and references therein, herein incorporated by reference. The methods to biotinylate the antibodies and attach them to the avidin coated beads are available to those skilled in the art.

The beads may be freed from the cells by digesting the peptide complexing agents with proteinase to remove the beads from the cell membrane. Then, one may obtain a bead size distribution using the Multisizer II and determine the number of large non-magnetic beads by peak integration. The number of N beads would be proportional to the number of MN cells.

Example 5

This Example illustrates a method for efficiently evaluating for the presence, absence, or amplification of nucleic acid sequences in a sample of nucleic acid. An example of the method is illustrated in FIG. 11.

In this method, the target nucleic acid can be DNA or RNA, single stranded or double stranded, fully purified, or as chromatin or chromosomes. Preferably, the nucleic acid would be extracted as purified nucleic acid (e.g., from cells) and evaluated as genomic or franctionated to segments of sizes, suitable for the particular evaluation being performed (e.g. by restriction enzyme digestion). The minimum length of the target nucleic acid is on the order of 10 bp (it has to be sufficiently long for near unique hybridization). There is no maximum limit for the length of the target nucleic acid, i.e., it could be the whole genome.

Materials:

(A) Probes. Nucleic acid probes are made that are complementary to specific regions of the target nucleic acid to be evaluated. The individual probes can be of various lengths (typically 50 bp to 1000 bp) and each probe with two complexing agents, typically incorporated into the nucleic acid probe by available nick translation methods.

(B) Antibodies. Antibodies are biotinylated and complexed with streptavidin-coated microspheres. The biotinylation includes a spacer between the antibody and the biotin molecule to limit interference with antibody-antigen binding.

(C) Microspheres. Microspheres (typically, 1 to 20 $\mu$m diameter polystyrene beads) are coated with streptavidin. Each bead size would be coated with only one kind of complexing agent.

Methods:

(A) Extract nucleic acids (e.g., from cells) and process as desired using available methods.

(B) Insert-peptide-dUTP into probes by available nick translation methods.

(C) Hybridize the nucleic acid probes to the target nucleic acid in solution and purify to remove unhybridized probes.

(D) In separate solutions, attach the biotinylated antibodies to their respective beads (one kind of antibody for each bead size).

(E) Simultaneously, react the coated beads with the target DNA-probe complexes to attach the beads to their respective complexing agents on the probes.

(F) Place the solution into a vial coated with a unique complexing agent that complexes with the probes hybridized to the target DNA. After attachment to the vial surface, wash several times to remove unattached beads.

(G) Separate the beads from the nucleic acid by protease treatment and quantify size spectrum using a Multisizer II (Coulter, Inc.)

(H) The number of beads of a particular size would be proportional to the number of target sequences in the nucleic acid sample. Hence, e.g., gene amplification would result in more beads of a particular size than expected from a control sample. Similarly, Downs Syndrome (an extra chromosome 21) would result in 50% more beads attaching to probes complementary to chromosome 21. In contrast, a deletion of a particular target sequence would result in fewer beads than expected. Using many different bead sizes would permit the evaluation of many target nucleic acid sequences simultaneously by using calibration curves, one for each target sequence, to translate the number of beads in each peak into the concentration of the corresponding target sequence in the sample.

Example 6

In this example, we describe results using our particle analysis assay to rapidly quantify bcr/abl chromosomal fusions in genomic DNA extracted from a human chronic myelogenous leukemia cell-line. It is demonstrated that our assay makes possible very rapid and low cost quantification of rearrangements in genomic DNA without the need for cell culturing, microscope scoring, or sequence amplification. The assay requires only seconds to "score" the number of chromosomal translocations typically taking weeks or even months of very costly technician time by available cytogenetic methods. The principle of the assay is to use the diameter of microparticles as the detectable marker in a sandwich-type assay and the number of such particles as the quantitative measurement. The position of particle attachment to the target DNA can be selected by the sequences of the hybridization probes and the unique complexing agents on the particles. The "scoring" of these detectable markers is accomplished by automated size-distribution analysis that requires only 10 to 15 seconds per sample regardless of how many cell-equivalents are being evaluated.

The particle analysis assay was used to detect $Ph^1$ chromosome translocations in isolated genomic DNA from a human CML cell line known to be $Ph^1$ positive, K-5628, and from a control cell line (H-1395) known to be $Ph^1$ negative (American Type Culture Collection, ATCC Cell-Line Number CRL-5868, http://www.atcc.org; M. R. Speicher et al., 80 Laboratory Investigation 1031–1041 (2000)). Commercially-available painting probes for the bcr/abl fusion region were used to capture the target sequences on the solid support surface (in this case, magnetic beads) and to attach the 5.7 $\mu$m diameter non-magnetic particles used here for quantification. The probe hybridization cocktail contained digoxigenin-labeled bcr probe and biotinylated abl probe. Following simultaneous hybridization of the probes to the genomic target DNA, the beads were added to the solution resulting in the anti-digoxigenin-coated magnetic beads complexing with the bcr probes and the streptavidin-coated non-magnetic beads complexing with the abl probes. This was followed by magnetic separation to remove unattached non-magnetic beads, DNase treatment to cut the fusion DNA connecting the magnetic and non-magnetic beads, another magnetic separation step to remove the magnetic beads, and then the acquisition of a particle-size spectrum and counting the number of 5.7 $\mu$m particles. The magnetic beads were removed, in this case, because their size distribution was very broad and would have interfered with the size distribution of the non-magnetic particles used here for detection. In practice, removal of the magnetic beads would not be required because their size distribution would be selected to prevent interference with the size distribution of the non-magnetic particles. For the present evaluation, these particular magnetic beads were used simply because they were available commercially with anti-digoxigenin coating.

Figure 12:
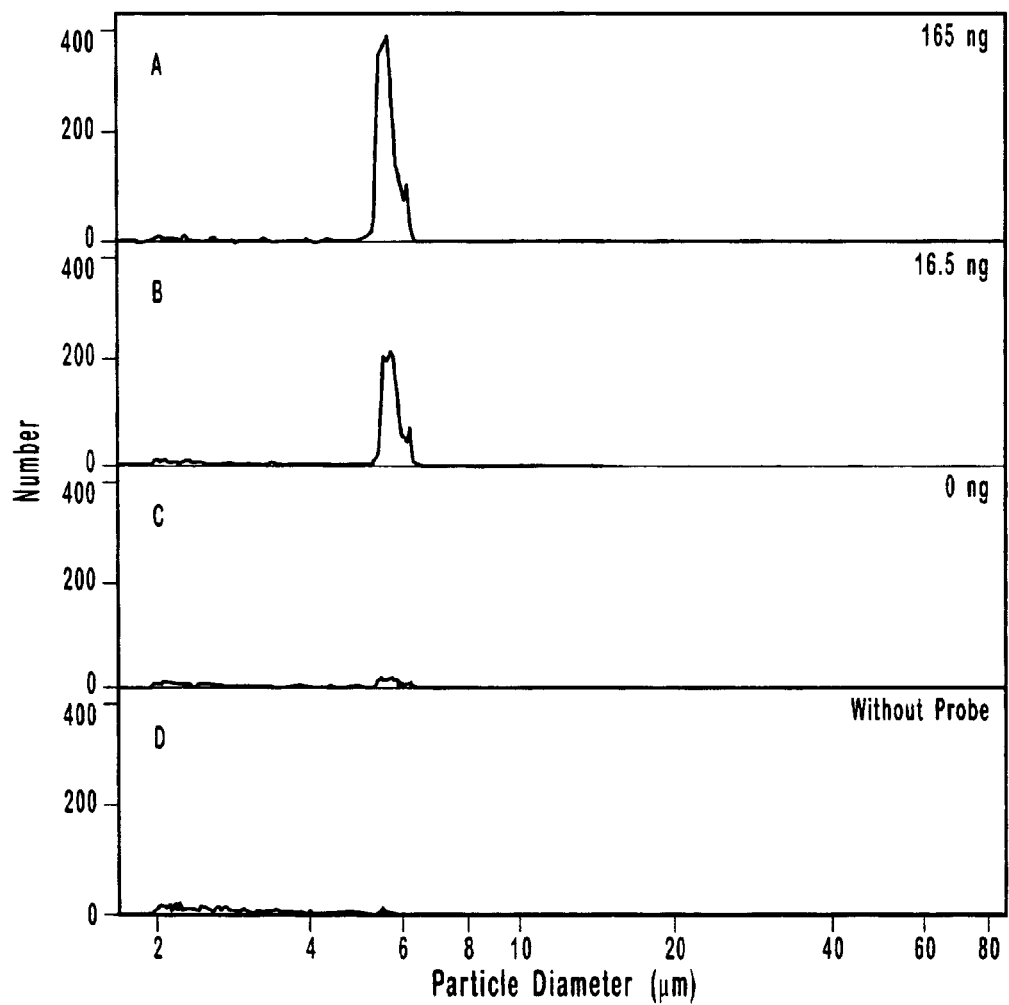

Particle-size spectra obtained using this method are illustrated in FIGS. 12A–D. The number of particles counted are presented as a function of particle diameter. The total number of particles of a particular size (in this case, the observed peak) is obtained automatically by integration using a computer interface with the particle counter. It is observed in FIG. 12 that the level of background noise outside the peak is relatively low resulting in a high signalto-noise ratio. It is also observed that the size of the peak decreases with decreasing target DNA (i.e., decreasing number of bcr/abl fusions) present in the sample solution. The result in FIG. 12A was obtained using 165 ng genomic DNA from the human CML cell line. A single large peak is observed with a mean diameter of 5.7 μm. This peak is composed of the non-magnetic microparticles recovered after hybridization and magnetic separation. In FIG. 12B, a smaller peak is observed at 5.7 μm particle diameter. This peak includes the non-magnetic microparticles recovered using 16.5 ng target DNA. In FIG. 12C, the hybridization solution contained only probes and beads, but no genomic DNA from the CML cells. In this case, only a very small The numerical results are presented in Table II. These values are the integrals of the peaks. The genomic K-562 DNA per 500 μl sample analyzed were 0, 0.165, 1.65, 16.5, and 165 ng. Given that the K-562 cells are essentially triploid8, the number of cell-equivalents per sample ranged from 0 to 18,000. Also, based on the frequency of $Ph^1$ chromosomes in this cell line8, we estimate that the bcr/abl fusions would range from 0 to 2700 per sample. It is observed that there is a clear relationship between the number of beads counted per sample and the number of expected bcr/abl fusions in the sample. It appears from these initial results that on the order of 1 microparticle is counted per bcr/abl fusion in the sample.

TABLE II

Quantification of $Ph^1$ fusions in human genomic DNA.

| Genomic DNA per sample (ng) | # cell equivalent | bcr/abl probe per sample (μl) | Expected number of $Ph^1$ in sample[a] | Number of beads counted per sample[b] | Counting time per sample (sec) |
|---|---|---|---|---|---|
| K-562 cells[c] | | | | | |
| 165 | 18,000 | 0.5 | 2700 | 1430 ± 38 | 12.8 |
| 16.5 | 1800 | 0.5 | 270 | 779 ± 28 | 12.7 |
| 1.65 | 180 | 0.5 | 27 | 151 ± 12 | 12.8 |
| 0.165 | 18 | 0.5 | 2.7 | 138 ± 12 | 12.7 |
| 0[d] | 0 | 0.5 | 0 | 108 ± 10 | 19.1 |
| 16.5[e] | 1800 | 0 | 270 | 49 ± 7 | 12.6 |
| H-1395 cells[c] | | | | | |
| 16.5 | 2700 | 0.5 | 0 | 58 ± 8 | 12.8 |
| 0[d] | 0 | 0.5 | 0 | 53 ± 7 | 12.9 |
| | | Separated magnetic beads only[f] | | 17 ± 4 | 12.6 |
| | | Saline only[g] | | 0 | 12.8 |

[a]Based on 15% $Ph^1$ chromosome frequency in the K-562 cell culture used here[g].
[b]Mean ± 1 s.d. based on counting statistics only.
[c]Cells are described under experimental protocol.
[d]Repeated the procedure as above, but without genomic DNA.
[e]Repeated the procedure as above with 16.5 ng genomic DNA, but without probe.
[f]Magnetic beads were placed in a saline solution without DNA, probes, or non-magnetic beads. The magnetic beads were then removed by magnetic separation and the residual number of beads in the relevant interval counted. The initial number of magnetic beads were the same as in all of the above measurements.
[g]Pure saline solution was counted, without any beads or other reagents present.

peak is observed at 5.7 μm. Although small, the fact that a detectable peak exists at all in this size interval indicates that some of the microparticles must have become attached to the magnetic beads during the hybridization procedure even though target DNA was not present. In order to determine how the particles may have become attached, we performed an experiment where all conditions were identical to those in FIG. 12B except that we did not include probes. These results are seen in FIG. 12D and show that the peak in FIG. 12B disappeared when the probes were not included. Based on these results, it is clear that the non-unique-sequence "painting" probes used here for abl and bcr exhibit some non-specific inter-probe hybridization, which resulted in some, albeit small, cross-attachment of magnetic and non-magnetic beads. Importantly, it is expected that this can be eliminated or at least substantially reduced by using unique-sequence probes. The small "background" seen in FIG. 12D from ~2 μm to about ~8 μm is the residual from the broad size distribution of the magnetic beads used for these experiments. As mentioned above, the magnetic beads would not be present in the non-magnetic particle interval if they were selected to have a non-overlapping size distribution.

The results in Table II also include several controls. When K-562 DNA was not present in the sample, then 108 particles were counted in the 5.0–6.8 μm diameter interval. As indicated above, we believe that these beads resulted from non-specific hybridization between the commercial painting probes used here as well as from residual magnetic beads that were not fully removed by the second magnetic separation step. This conclusion is supported by the 49 beads observed when no probes were present in the K-562 experiment suggesting that the probe—probe non-specific hybridization contributed about half of the 108 beads observed. We have also observed that the number of residual magnetic beads remaining after magnetic removal can vary somewhat between experiments and can account for a substantial fraction of the 49 beads observed without probes. Seventeen beads were observed in the 5.0–6.8 μm interval following the separation of magnetic beads alone, i.e., without the presence of probes, DNA, or non-magnetic beads. These were residual magnetic beads that remained after the magnetic bead removal step. Taken together, it appears that the background level for the PCA is on the order of 100 particles when using commercially available painting probes and the magnetic beads employed here. Given that the background of the counting instrument itself (using pure saline) is essentially zero in the relevant size interval, it is expected that substantial reductions in background are possible by using unique-sequence probes instead of the "painting" probes employed in the present experiments and by using magnetic beads (or other solid support) that will not interfere with the size distribution of the non-magnetic particles.

Also presented in Table II are results for a human cell line (H1–1395) which does not have $Ph^1$ chromosomes. Genomic DNA from these cells was used to measure the non-specific hybridization between the bcr/abl probes used here and human genomic DNA. In this case, we repeated the 16.5 ng DNA measurement by adding H-1395 genomic DNA instead of K-562 genomic DNA in the sample. We also included a simultaneous control, i.e., no genomic DNA. The results are clear. Only 58 beads were counted when we used H-1395 DNA compared with 779 beads counted when we used K-562 DNA. This demonstrates that non-specific hybridization is relatively low and contributes less than 8% of the beads counted with 16.5 ng genomic DNA. Given that 53 beads were counted with probe alone, most of this 8% was actually from inter-probe hybridization. This is consistent with the 3:1 probe-to-genomic DNA in the sample.

The counting times per sample are also listed in Table II. These counting times should be compared with the efforts required for microscopic analysis of cytogenetic preparations. The sample measured here of 165 ng genomic DNA is equivalent to about 18,000 cells. Using FISH cytogenetics, a technician typically scoring about 200 cells per day would require about 4 months to score 18,000 cells. In contrast, our bead counting method completed the "scoring" in only 12.8 seconds. Clearly, this dramatic advance in the quantification speed of chromosomal rearrangements opens new possibilities in medicine, health, and research hitherto not possible due to the inefficiencies and inadequacies of available assays.

Finally, the PCA approach has many other potential applications as well. For example, multiple nucleic acid rearrangements could be quantified in the same sample simultaneously by selecting beads of various diameters, each diameter representing a particular type of rearrangement. This would result in several peaks in FIG. 13A, each peak with a different mean particle diameter. Also, random inter-chromosomal rearrangements, such as may be caused by certain environmental agents, could be rapidly quantified by using a cocktail of whole-chromosome painting probes, each probe complementary to a different chromosome. In this case, the largest chromosomes would preferably be used to maximize the fraction of the genome evaluated. Because of it's intrinsic quantitative nature, the PCA method should also be a powerful tool for the detection of more subtle alterations such as deletions, gene amplifications, and a variety of other genetic abnormalities. We have also shown that the PCA method can be used to quantify specific proteins. For protein detection, the complexing agents are antibodies instead of nucleic acid probes and the microparticles are used as the detectable marker instead of, for example, a radioisotope in the case of radio-immunoassays (RIAs). It is instructive to note that automated particle counting detects 100% of the detectable marker in the sample in about 13 seconds while scintillation counting of a radiolabel such as $^{125}I$ would require 40 days (the radiological half life of $^{125}I$) to detect at most 50% of the marker. Furthermore, as with DNA rearrangements, the PCA approach can be used to quantify multiple proteins simultaneously in a single sample by generating a spectrum of different size particles, each size unique for a particular protein.

Experimental Protocol

Target DNA. Genomic DNA from two different human cell lines were used in these experiments. Purified genomic DNA from the K-562 human chronic myelogenous leukemia cell-line was purchased from the American Type Culture Collection (ATCC; Rockville, Md.). These cells have been determined to contain an average of about 69 chromosomes per cell and have a Ph1 chromosome frequency of =15% (Culture B in ref. 8). Purified genomic DNA from the H-1395 human lung adenocarcinoma cell-line was also purchased from ATCC. This is a near-normal cell-line without any apparent Ph1 chromosomes (American Type Culture Collection, ATCC Cell-Line Number CRL-5868, http://www.atcc.org; M. R. Speicher et al., 80 Laboratory Investigation 1031–1041 (2000)).

Probes. The m-bcr/abl (minor breakpoint, Catalog Number P5120) translocation DNA probe was obtained from Ventana Medical Systems, Inc. (Tucson, Ariz.). The probe is a mixture of digoxigenin-labeled DNA probes specific for the minor breakpoint region of the bcr locus on chromosome 22, and biotin-labeled DNA probes specific for the abl locus on chromosome 9. The probes specific for the m-bcr gene are proximal to the translocation breakpoint on chromosome 22 and the probes specific for the abl gene are distal to the translocation breakpoint on chromosome 9. The DNA probe solution is premixed with blocking DNA in 50% formamide and 2×SSC.

Microparticles. The streptavidin-coated non-magnetic particles (5.7 $\mu$m diameter, s.d. ±0.3 $\mu$m) were purchased from Bangs Laboratories, Inc. (Fishers, Ind.). These were monodisperse polystyrene microspheres suspended in a stock solution of 9.4×107 beads per mL. The anti-digoxigenin-coated magnetic particles (about 1 $\mu$m mean diameter, but with a broad distribution of sizes) were purchased from Roche Molecular Biochemicals (Indianapolis, Ind.). These were superparamagnetic polystyrene particles with no residual magnetism of the particles after removal of the magnet. The magnetic particles were suspended in a stock solution of 1.5×1010 particles per mL.

Hybridization. A 10 $\mu$l solution consisting of 3.3-$\mu$g genomic DNA in Tris buffer was added to 40 $\mu$l of denature solution with final concentration of 70% (vol/vol) formamide and 2×SSC. This solution was heated to 70° C. in a water bath for 5 min and then transferred to a 30 $\mu$l hybridization solution containing 10 $\mu$l probe. The final hybridization solution contained 50% (vol/vol) formamide, 2×SSC, 1% (vol/vol) salmon sperm DNA (Sigma, St. Louis, Mo.), and 1% (vol/vol) SDS (10% Sodium dodecyl sulfate solution, Sigma, St. Louis, Mo.). The mixture was then incubated with gentle agitation overnight at 40° C. in a Lab-Line Environ-Shaker.

Particle attachment to probes. After hybridization, 200 $\mu$l TE buffer (10 mM Tris-HCl, pH 7.5; 1 mM EDTA) and 230 $\mu$l B&W buffer (2 M NaCl; 10 mM Tris-HCl, pH 7.5; 1 mM EDTA) were added to the sample and then 25 $\mu$l of magnetic particle solution and 75 $\mu$l non-magnetic particle solution were added. The magnetic particles were pre-washed with B&W twice and the non-magnetic particles with B&W/TE (1:1 vol/vol) twice. The mixture was rotated gently at room temperature for 1 h.

Magnetic separation. The magnetic particles, and those non-magnetic particles cross-linked with magnetic particles via hybridization to the same contiguous target DNA sequence, were collected with a magnetic particle concentrator (MPC, Dynal, Inc, Lake Success, N.Y.) and the supernatant was removed. The particles collected were washed once with 1×SSC, 0.2% SDS solution and once with 0.1×SSC, 0.2% SDS solution (10 min each), followed by washing with B&W three times and TE once, each with 200 µl.

Particle counting. The magnetically separated particles were digested using DNase I (Gibco BRL, Grand Island, N.Y.) according to the manufacturer's protocol to detach all particles that may be cross-linked by hybridization. The magnetic beads were collected by MPC and the supernatant transferred to a counting cuvette (Beckman Coulter, Inc, Miami, Fla.) containing Isoton II diluent (Beckman Coulter, Inc, Miami, Fla.). Final volume was 10 mL. The particles remaining in the solution were counted using a Coulter Multisizer II (Beckman Coulter, Inc, Miami, Fla.). The measurement volume was 500 µl.

Example 7

This new technology can be used to quantify many different kinds of target molecules simultaneously and can be used to detect any molecule for which there exists two non-cross reacting complexing agents. For example, proteins of importance in health and nutrition such as ferritin, transferrin, transferrin receptor, folic acid, vitamin-B12, vitamin-A retinol binding protein, insulin, cortisol, estradiol, FSH, LH, progesterone, T3, T4, and TSH have two commercially available antibodies that bind to different sites on the same molecule and would therefore be detectable individually or simultaneously using the present method. Antibodies have been developed for a large number of other molecules as well which can also be quantified using the present method. In addition, modern antibody production can now be used to develop low-cost antibodies against almost any desired target molecule.

The protein separation and quantification technology is illustrated in FIG. 13. For the detection of proteins, one antibody type (preferably a monoclonal antibody) would be attached to a solid support, e.g., to the surface of a superparamagnetic microbead (M), and another antibody type (usually a polyclonal antibody attaching to several sites on the same protein) attached to the magnetically non-responsive microbeads (N). In this example, the antibodies are coated directly onto the surface of carboxylic acid coated beads. Other attachment methods are also possible such as biotin/avidin, digoxygenin/anti-digoxygenin, and other antibody/antigen complexing reactions.

We have successfully performed experiments using our Particle Analysis Assay to detect protein ferritin. We performed our initial tests using this protein because it is very important in the evaluation of iron status in humans. Our results of separation and particle size distribution analysis are illustrated in FIG. 14. Two peaks are seen, one with a mean particle diameter of 2.8 µm (the super-paramagnetic beads) and another with a mean particle diameter of 4.45 µm (the magnetically non-responsive beads). It is clear that these two peaks are easily resolved and that a much larger number of peaks could also be resolved. The total number of beads of each kind can be obtained from the integral of each peak. In this case, there were a total of 808 non-magnetic beads observed in a 0.5 mL aliquot of the 10 mL final sample solution. This translates into a total of 808×20=16,160 non-magnetic beads recovered following the magnetic separation step. Based on a total of 0.27 µg ferritin in the initial test solution, we calculate a proportionality constant of $3.75 \times 10^{-17}$ mole of ferritin per non-magnetic bead recovered. The minimum detection limit of this method is only a few beads. For identical protocol conditions, this calibration constant could be multiplied by the number of non-magnetic beads recovered from an unknown sample of ferritin to obtain the ferritin concentration in the unknown sample from the number of non-magnetic beads counted in the unknown sample.

Experiments were also performed to measure the number of counts in the relevant size windows when ferritin was not present in the solution. FIG. 15 shows that when ferritin is not included the peak for non-magnetic beads is not present, demonstrating that there is no detectable non-specific cross-reactions between beads.

Based on these results, and the fact that we have not yet optimize and fine tuned the method, we estimate the detection limit for this method to be in the amole range, considerably lower than available radio-immunoassays and ELISAs, which are typically in the pmole to fmole range.

Experimental Protocol

Coat beads with ferritin-specific antibodies. Magnetically-responsive beads (Dynabeads M-270) with carboxylic acid surface coating (Catalog #A143.05) were purchased from Dynal A/S, Oslo, Norway. These were 2.8 µm mean diameter microspheres in $2 \times 10^9$ beads per mL stock solution. Suspend First, the Dynabeads M-270 were fully suspended in the stock solution by pipetting and vortexing for 1 min. Immediately pipette 100 µl into a 1.5 mL Eppendorf tube. Place the tube in a Dynal magnet stand (MPC) for 4 min and remove the supernatant. Resuspend beads in 100 µl of 0.01 M NaOH. Mix well for 5 min and repeat once. Wash beads twice with 100 µl of 0.1 M MES (2-[N-morpholino]ethane sulfonic acid) buffer pH 5.0 and once 100 µl of cold Milli-Q water. Add 200 µl of 0.005 M CMC (N-cyclohexyl-N-(2-morpholinoethyl)carbodimde methyl-p-toluensulfonate) in cool Mili-Q water to beads and vortex to mix properly. Incubate for 10 min at 4° C. with slow tilt rotation. Remove supernatant using magnet stand. Add 120 µl of 0.005 M CMC (Catalog #C1011, Sigma) and 80 µl of 0.3 M MES (Catalog #M2933, Sigma). Vortex and incubate as above for 30 min. Wash beads twice with cold 200 µl of 0.1 M MES as quickly as possible. Resuspend Dynabeads M-270 in 150 µl of 10 mM MES containing 60 µg of monoclonal anti-ferritin (Catalog #M94157, Fitzgerald Industries International, Inc, Concord, Mass.). Vortex to ensure good mixing of protein and beads. Incubate for 20 min at 4° C. with slow tilt rotation. Add BSA (Sigma) to final concentration 0.1% and incubate as above for 4 h. Wash with 120 µl of PBS containing 0.1% BSA and 0.1% Tween 20 (Sigma) four times. Resuspend beads in 200 µl of PBS with 0.1% BSA, 0.1% Tween 20, and 0.02% $NaN_3$ and store at 4° C.

Non-magnetically-responsive beads (carboxylic acid coated polystyrene beads, Catalog #PC05N, Lot #1193) were purchased from Bangs Labs, Fishers, Ind. These were 4.45 µm mean diameter microspheres in $1.988 \times 10^9$ beads per mL stock solution. The protocol for coating the Bangs beads with antibody was the same as described above for the Dynabeads M-270 with the exceptions that the Bangs beads were coated with polyclonal anti-ferritin (Catalog #70-XG50, Fitzgerald Industries International, Inc, Concord, Mass.) and employed centrifugation for the washing steps instead of the Dynal magnet stand.

Magnetic separation. Mix well 2 million (2 µl) monoclonal antibody coated Dynal beads with 0.27 µg ferritin (Catalog #30-AF10, Fitzgerald Industries International, Inc, Concord, Mass.) in TBST (10 mM Tris, 50 mM NaCl, and 0.1% Tween 20, pH 7.5) buffer (total 150 µl). Rotate gently at room temperature (r. t.) for 1 h. Wash with 150 µl of TBST three times using Dynal magnet stand (4 min each). Mix with 2 million (2 µl) polyclonal coated Bangs beads in 150 µl of TBST. Again, rotate gently at r. t. for 1 h. Wash with B&W 4 times and TE once using Dynal magnet stand (4 min each). Digest with 1 µl Proteinase K (from 23 mg/mL stock solution, Catalog #P2308, Sigma) in 150 µl of 0.01 M Tris and 0.005 M EDTA at 40° C. for 4 hours. Place tube into Dynal magnet stand (2 min) and transfer supernatant into Beckman-Coulter counting cuvette (Catalog #8320592). Wash the tube 3 times with saline (Isoton II, Beckman-Coulter, Inc.) and then dilute with Isoton II diluent (Beckman Coulter, Inc.) to 10 mL. The same procedure was followed for the control experiment except that ferritin was not added to the solution.

Particle size analysis and bead counting. Obtain particle size distribution for the beads that remain in the solution using the Coulter Multisizer II (Beckman-Coulter, Inc) It is seen in FIG. 14 that the number of non-magnetic particles is readily obtained and the concentration of the target protein (ferritin in this example) can be quickly determined from the number of non-magnetic beads using standard calibration data. For example, the non-magnetic beads counted in FIG. 14 result in $3.75 \times 10^{-17}$ mole of ferritin per non-magnetic bead recovered. For identical protocol conditions, this calibration constant could be multiplied by the number of non-magnetic beads recovered from an unknown sample of ferritin to obtain the ferritin concentration in the unknown sample from the number of non-magnetic beads counted in the unknown sample.

Multiple Molecular Detection and Quantification using the Method of the Present Invention Target Molecules (antigens): Ferritin, transferrin receptor, TSH, retinol binding protein, and folic acid. In human bood serum.

Microbeads: Beads of different sizes and with various chemical and physical functional surfaces are available commercially (e.g. Dynal AS, and Bangs Labs, Inc.). Beads of different diameters can be selected to serve as unique identifiers for each of the five target molecules. The various chemical and physical functional surfaces provide the opportunity for selecting and optimizing bead-antibody immobilization strategies. A preferred approach is to use streptavidin-coated beads as the basic substrate upon which the selected biotinylated antibodies can be attached.

The magnetically-responsive (M) beads can be Dynabeads M-280, 2.8 µm mean diameter. These beads are commercially available with streptavidin surface coating from Dynal AS, Oslo, Norway.

The non-magnetic (N) beads can be selected to be five different diameters, one diameter for each of the five target molecules. For this example, bead diameters in the 4 to 20 µm range, (a much broader range of sizes can be used) would be selected to eliminate significant overlap of the peaks. Streptavidin coated beads of these sizes (and almost any other diameter if special order) are available commercially from Bangs Labs, Fishers, Ind. The main selection criterion for bead size is to make sure that we can adequately resolve the peaks in the measured bead size distribution. We have performed several experiments with various size beads from Bangs Labs that provide assurance that the bead sizes selected here should be resolvable.

Antibodies: The antibodies used in this example would be obtained from commercial vendors. Monoclonal and polyclonal antibodies for ferritin, transferrin receptor are available from Fitzgerald Industries International, Inc, Concord, Mass. A monoclonal antibody for retinol binding protein is available from Fitzgerald. A polyclonal antibody for retinol binding protein is available from US Biological, Swampscott, Mass. Both monoclonal and polyclonal antibodies for TSH are available from Fitzgerald. Monoclonal and polyclonal antibodies for folic acid are also available from Fitzgerald.

Biotinylation of Antibodies: A biotin molecule would be conjugated with each antibody using a "BiotinTag Micro Biotinylation Kit" (B-TAG) from Sigma chemical company. It should be noted that this procedure also adds a 12 atom spacer between the biotin molecule and the antibody to facilitate protein binding. Briefly, the biotinylated antibodies would be synthesized by adding 10 µL (5 µg/µL) of Biotinamidocaproate-N-hydroxysulfosuccinimide ester (BAC-SulfoNHS) in 0.1 M sodium phosphate buffer, pH 7.2 to 0.1 mL of antibody (10 mg/mL) in same sodium phosphate buffer. Then, reacted for 2 hours with gentle shake at 4° C. The biotinylated antibody will then be purified by applying the biotinylation reaction mixture to a pretreated Micro-spin column G-50 packaged with Sephadex G-50. Spin the column for 2 min at 700×g. The purified sample is collected at the bottom of the support tube. Place the column into another tube and add 0.2 mL PBS (0.01 M, pH 7.4). Spin the column for 1 min at 700×g and repeat. Pool the fractions containing the purified antibody which is now ready to use.

Immobilizing Antibodies on Beads: To immobilize the biotin-labeled antibodies on the streptavidin coated beads, the beads are first washed with PBS twice and suspended in the same buffer (0.5 mg beads per mL PBS buffer). To this solution, we will add 5 µg biotinylated antibody and then react at room temperature (~22° C.) for 30 min with gentle mixing. The beads will then be washed three times with PBS and resuspended in the same buffer for use.

NOTE: The preceding bead and antibody preparations can all be done in advance, and for commercial applications, would be part of a kit. The separation and detection steps listed below can be simplified and some steps (e.g., incubation) shortened substantially.

Magnetic Separation: React the antibody-coated magnetic beads with the target antigen (for this example, with human serum). This is accomplished as follows: To antigen-containing matrix (0.5 mL), add 0.25 mg/0.5 mL (PBS buffer supplemented with 0.2% BSA) magnetic beads, and incubate for 1 hour at room temperature. Collect the beads with a magnetic particle concentrator (MPC) and wash three times with PBS. Resuspend the beads with 0.5 mL of the same buffer. To this solution, add non-magnetic beads coated with the second antibody (0.25 mg/0.5 mL, PBS buffer supplemented with 0.2% BSA) and incubate for 1 hour at room temperature. Collect the magnetic beads with MPC and wash 5 times with buffer. In this procedure, non-magnetic beads are removed by the magnetic washes except those that crosslink with the magnetic beads through antibody-antigen-antibody coupling. The beads are then suspended in 0.5 mL PBS. Note that separation could also be done using a solid support surface other than magnetic beads, e.g., the inside of a microtiter well, as taught in the body of the patent.

As an example, the separation from human serum of ferritin, transferrin receptor, TSH, retinol binding protein, and folic acid, is accomplished using the magnetic separation procedure described above. In this case, 100 µL serum is diluted (1/10) with phosphate buffer saline total 1 mL (pH 7.2 containing 0.5 mL/L Tween 20). To this solution are added Dynal beads, each with only one of the five kinds of monoclonal antibodies used in this project (0.25 mg beads/ 25 µl PBS). The mixture is incubated for 1 hour at room temperature with gentle rotation. Collect the beads with a magnetic particle concentrator (MPC) and wash three times with PBS. The beads are resuspended with 1 mL of the same buffer supplemented with 0.1% BSA. To this solution are added non-magnetic beads coated with a polyclonal antibody, in this case a unique bead size for each kind of antibody (0.3 mg beads/0.3 mL), and incubated for 1 hour at room temperature. Collect the complexes with MPC and wash with buffer five times. In this procedure, non-magnetic beads are removed by multi-wash except those that crosslink with the magnetic beads through antibody-antigen-antibody coupling. The beads are then suspended in 0.5 mL PBS. The proteins on beads are then cut by use of proteinase K (15 µL from 23 mg/mL stock solution), then diluted with Isoton II diluent (Beckman Coulter Counter) to 10 mL and analyzed using the Coulter Multisizer II. Initially, we will perform the magnetic separation and non-magnetic bead attachment in two separate steps. This approach will remove essentially all of the non-target proteins from the solution and hence reduce any possible non-specific reactions with the non-magnetic beads used here as our detectable marker.

Simultaneous Quantification of Target Molecules: Determine the target protein concentration by counting the number of non-magnetic beads after magnetic separation. The quantification of target protein concentration will be accomplished by digesting the proteins on the beads using proteinase K (2.5 µL from 23 mg/mL stock solution), allow to react for 30 min, and then dilute with Isoton II diluent (Beckman Coulter Counter) to 10 mL and size/count using the Coulter Multisizer II. Generation of a bead size distribution requires only 10 to 15 seconds.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. A method for separating a nucleic acid containing both a first nucleotide sequence type and a second nucleotide sequence type from a sample also comprising nucleic acids not containing both the first nucleotide sequence type and the second nucleotide sequence type, said method comprising:
   (a) coupling a first hybridization probe configured for hybridizing to the first nucleotide sequence type to a magnetically responsive first bead via a first pair of complexing agents to form a first probe-bead complex, and coupling a second hybridization probe configured for hybridizing to the second nucleotide sequence type to a magnetically non-responsive second bead, which is distinguishable from the first bead by size, charge, color, or attachability to a solid support, via a second pair of complexing agents to form a second probe-bead complex;
   (b) mixing the first probe-bead complex and the second probe-bead complex with the sample to form a mixture under conditions such that the first hybridization probe hybridizes to the first nucleotide sequence type and the second hybridization probe hybridizes to the second nucleotide sequence type;
   (c) separating the first probe-bead complex and nucleic acids hybridized to the first hybridization probe portion thereof from the first mixture by applying magnetic force to the mixture and then washing the isolated first probe-bead complex and nucleic acids hybridized to the first hybridization probe portion thereof, thereby obtaining a fraction comprising the first nucleotide sequence type;
   (d) separating the second probe-bead complex and nucleic acids hybridized to the second hybridization probe portion thereof from the fraction comprising the first nucleotide sequence type according to the properties of the distinguishable feature of the second bead and then washing to remove nucleic acids not hybridized to the second hybridization probe, thereby separating the nucleic acid containing both the first nucleotide sequence type and the second nucleotide sequence type from nucleic acids not containing both the first nucleotide sequence type and the second nucleotide sequence type.

2. A method for separating and quantifying a nucleic acid containing both a first nucleotide sequence type and a second nucleotide sequence type from a sample also comprising nucleic acids not containing both the first nucleotide sequence type and the second nucleotide sequence type comprising:
   (a) coupling a first hybridization probe configured for hybridizing to the first nucleotide sequence type to a magnetically responsive first bead via a first pair of complexing agents to form a first probe-bead complex, and coupling a second hybridization probe configured for hybridizing to the second nucleotide sequence type to a magnetically non-responsive second bead, which comprises a feature distinguishable from the first bead by size, charge, color, or attachability to a solid support, via a second pair of complexing agents to form a second probe-bead complex;
   (b) mixing the first probe-bead complex and the second probe-bead complex with the sample to form a mixture under conditions such that the first hybridization probe hybridizes to the first nucleotide sequence type and the second hybridization probe hybridizes to the second nucleotide sequence type;
   (c) separating the first probe-bead complex and nucleic acids hybridized to the first hybridization probe portion thereof from the mixture by applying magnetic force to the mixture for isolating the first probe-bead complex and nucleic acids hybridized to the first hybridization probe portion thereof and then washing the isolated first probe-bead complex and nucleic acids hybridized to the first hybridization probe portion thereof, thereby obtaining a fraction comprising the first nucleotide sequence type;
   (d) separating the second probe-bead complex and nucleic acids hybridized to the second hybridization probe portion thereof from the fraction comprising the first nucleotide sequence type according to the properties of the distinguishable feature of the second bead and then washing to remove nucleic acids not hybridized to the second hybridization probe, thereby separating the nucleic acid containing both the first nucleotide sequence type and the second nucleotide sequence type from nucleic acids not containing both the first nucleotide sequence type and the second nucleotide sequence type; and
   (e) determining the amount of nucleic acid containing both the first nucleotide sequence type and the second nucleotide sequence type as a proportion of total nucleic acids present in the sample.

3. A method for diagnosing a disease or disorder associated with the presence in an individual of a nucleic acid comprising a first nucleotide sequence type and a second nucleotide sequence type comprising:
   (a) coupling a first hybridization probe configured for hybridizing to the first nucleotide sequence type to a magnetically responsive first bead via a first pair of complexing agents to form a first probe-bead complex, and coupling a second hybridization probe configured for hybridizing to the second nucleotide sequence type to a magnetically non-responsive second bead via a second pair of complexing agents to form a second probe-bead complex;
   (b) obtaining a nucleic acid sample from an individual to be tested and mixing the first probe-bead complex and the second probe-bead complex with the sample to form a mixture under conditions such that the first hybridization probe hybridizes to the first nucleotide sequence type and the second hybridization probe hybridizes to the second nucleotide sequence type;
   (c) separating the first probe-bead complex and nucleic acids hybridized to the first hybridization probe portion thereof from the mixture by applying magnetic force to the mixture for isolating the first probe-bead complex and nucleic acids hybridized to the first hybridization probe portion thereof and then washing the isolated first probe-bead complex and nucleic acids hybridized to the first hybridization probe portion thereof, thereby obtaining a fraction comprising the first nucleotide sequence type; and
   (d) separating the second probe-bead complex and nucleic acids hybridized to the second hybridization probe portion thereof from the fraction comprising the first nucleotide sequence type according to the properties of the distinguishable feature of the second bead and then washing to remove nucleic acids not hybridized to the second hybridization probe, thereby separating the nucleic acid containing both the first nucleotide sequence type and the second nucleotide sequence type from nucleic acids not containing both the first nucleotide sequence type and the second nucleotide sequence type;

(e) detecting the presence of the nucleic acid containing both the first nucleotide sequence type and the second nucleotide sequence type; and (f) quantifying the nucleic acid containing both the first nucleotide sequence type and the second nucleotide sequence type, wherein the presence or increased presence of the nucleic acid containing both the first nucleotide sequence type and the second nucleotide sequence type supports a diagnosis of the presence of the disease or disorder, and wherein the absence or decreased presence of a nucleic acid containing both the first nucleotide sequence type and the second nucleotide sequence type supports a diagnosis of the absence of the disease or disorder.

4. A process for separating objects bearing at least a first binding site and a second binding site from other objects that do not bear both said first binding site and said second binding site, comprising (a) mixing a first binder/bead composition, comprising a magnetically responsive bead coupled to a first binder that binds the first binding site on said objects, and a second binder/bead composition, comprising a magnetically non-responsive bead coupled to a second binder that binds the second binding site on said objects, wherein said magnetically non-responsive bead comprises a feature distinguishable from the first bead by size, charge, color, or attachability to a solid support, with a fluid containing said objects and said other objects to form a mixture such that said first binder binds said first binding site to form a first complex and said second binder binds said second binding site to form a second complex;

(b) contacting said mixture with a magnetic field such that said first complex is attracted to said magnetic field and removing said first complex from said mixture to form a fraction; and (c) separating said objects from said fraction comprising said other objects by the size, charge, color, or attachability to a solid support that distinguishes the magnetically non-responsive bead from the magnetically responsive bead.

5. The process of claim 4 wherein said objects are selected from the group consisting of nucleic acids, proteins, chromosomes, cells, and organelles.

* * * * *

UNITED STATES PATENT AND TRADEMARK OFFICE
CERTIFICATE OF CORRECTION

| | | |
|---|---|---|
| PATENT NO. | : 6,994,971 B1 | Page 1 of 1 |
| APPLICATION NO. | : 10/089560 | |
| DATED | : February 7, 2006 | |
| INVENTOR(S) | : Tore Straume et al. | |

It is certified that error appears in the above-identified patent and that said Letters Patent is hereby corrected as shown below:

In column 45 line 27 please delete "from the first mixture" and replace it with --from the mixture--.

Signed and Sealed this

Seventeenth Day of October, 2006

JON W. DUDAS
*Director of the United States Patent and Trademark Office*

SEQUENCE LISTING

<160> NUMBER OF SEQ ID NOS: 10

<210> SEQ ID NO 1
<211> LENGTH: 880
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: "n" represents a, c, g, or t.
<220> FEATURE:
<221> NAME/KEY: misc_feature
<222> LOCATION: (837)..(837)
<223> OTHER INFORMATION: "n" represents a, c, g, or t.
<220> FEATURE:
<221> NAME/KEY: misc_feature
<222> LOCATION: (850)..(850)
<223> OTHER INFORMATION: "n" represents a, c, g, or t.
<220> FEATURE:
<221> NAME/KEY: misc_feature
<222> LOCATION: (876)..(876)
<223> OTHER INFORMATION: "n" represents a, c, g, or t.

<400> SEQUENCE: 1

```
tngttctcca gcttgcatgc ctgcaggtcg acgccctag atctgtctcc taaaatggct      60
ccccagacac agcacagtgt tcctggggtc gttcaggacg gaaggcagcg gcgccccccc    120
ccaatctttg catgtcttgg gatgcaaaac aatttcccca ccttctctct gctcacccca    180
ccgaccgtcg cccctaaagt gaagtctgct ggctgccgaa aagggaaatg gaaggagga    240 accattcaag ttcaacgaca tggcgacggc agctccggcg ggagccgcgc tttggcaggg    300
gagggtgcgc catctgcagc agcgcgctag cacatagggg aagggcgat gggccccct     360 ccacgcctta gcgtgcaact cgcccccata ttctccccac agcattcatc cttgacccaa    420
cccgctttgc tctttagccc cagctctctg ctttggtcat caccccgaaa acctatgaaa    480
atccagagcc cctgcacccg cgcgttccgc tagagaacct accgtgaaga cccgagcgtt    540
gtgtccttgt ccttgcttat tcgatcctac ttgaaacact ggcagcactc acggccttcg    600
gggctcggcc agcagcttcc gagaacgata gctttcttgc gcagcgcgta gacgcgatgc    660
```

```
ggtaattttg agccacccaa gataagacac taacttgacc ttaactttgt cagggcgccc      720
ctggtatctg gagaacgtga acagacactt gtctggcagc ttctcgtaaa aactgactgg      780
ggaagggatt ctgagtcatt tcatttatta ccccttacaa gttttgcaag aaaagcnttt      840
tcttccttgn ccaaacttta attattttat tgctcntttt                            880
```

<210> SEQ ID NO 2
<211> LENGTH: 795
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(5)
<223> OTHER INFORMATION: "n" represents a, c, g, or t.
<220> FEATURE:
<221> NAME/KEY: misc_feature
<222> LOCATION: (8)..(8)
<223> OTHER INFORMATION: "n" represents a, c, g, or t.
<220> FEATURE:
<221> NAME/KEY: misc_feature
<222> LOCATION: (13)..(13)
<223> OTHER INFORMATION: "n" represents a, c, g, or t.
<220> FEATURE:
<221> NAME/KEY: misc_feature
<222> LOCATION: (757)..(757)
<223> OTHER INFORMATION: "n" represents a, c, g, or t.

<400> SEQUENCE: 2

```
ttnnnttntt cgnctcggta cccggggatc tctagagtc gacgcggccg cggaattaac       60
cctcactaaa gggaacgaat tcggatctac cttctgaaga ccagagaacc cctggggaat     120
tgccccgccc ctttaaggaa acctcctaca cagagagctt tggtaattgt tcatggttta     180
tacttatctc caataatgga tgtcatgggg ggttgaaagt tttgcataac cggttttttt     240
tttcttcatg ttacctgtct tatttaaagg caggcctacc tcaaaaacat tacaccagtg     300
gaggagagag agagagagag agagagagag agagagagag agagttacat tgttgaaaa     360 aatagtcatt tcatatcctt tccagaaagg agaggatgaa attagaaatg gacccagttt     420
tcagtttctg atatcttcaa agtaccatca ccaagaacaa gaacactcag acaaaaatct     480
aacccaaacc ccatgccttc aaagggcatc ttccacctat gcgaagggca tgccaaattt     540
ttaagattgg gagtgaggtg acatacagga aaaaatttct ctgtattacc caaaagaaa     600 gttttgctgg caagaatgat gtaaacaaag caagggcatt ttcttttcct cctttttcttt    660 ttctccttcc ttcctttctt ccttccttcc ttccttcctt ccttccttc ttacttcttt     720 ctttctttct ttcttctttc tttctttctc ctggggnggg ggtagactgc caaactaagt    780
atttgtttct tgtaa                                                     795
```

<210> SEQ ID NO 3
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 3

```
tgccttccgt cctgaacgac cccaggaaca ctgtgctgtg tctggggagc                 50
```

<210> SEQ ID NO 4
<211> LENGTH: 50
<212> TYPE: DNA
<213> ORGANISM: Artificial Sequence

```
<220> FEATURE:
<223> OTHER INFORMATION: Synthetic oligonucleotide

<400> SEQUENCE: 4
cggcagccag cagacttcac tttaggcgcg acggtcggtg gggtgagcag            50

<210> SEQ ID NO 5
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 5
gctgcagatg gcgcaccctc ccctgccaaa gcgcggctcc cgccggagct            50

<210> SEQ ID NO 6
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 6
gggttgggtc aaggatgaat gctgtggcga gaatatgggg gcgagttgca            50

<210> SEQ ID NO 7
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 7
cgaattcgga tctaccttct gaagaccaga gaacccctgg ggaattgccc            50

<210> SEQ ID NO 8
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 8
catggtttat acttatctcc aataatggat gtcatggggg gttgaaagtt            50

<210> SEQ ID NO 9
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 9
agtcatttca tatcctttcc agaaaggaga ggatgaaatt agaaatggac            50

<210> SEQ ID NO 10
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 10
tcagacaaaa atctaaccca aaccccatgc cttcaaaggg catcttccac            50
```